(12) United States Patent
Ho

(10) Patent No.: US 6,831,279 B2
(45) Date of Patent: Dec. 14, 2004

(54) LASER DIODE-EXCITED BIOLOGICAL PARTICLE DETECTION SYSTEM

(75) Inventor: Jim Yew-Wah Ho, Medicine Hat (CA)

(73) Assignee: Her Majesty the Queen in right of Canada, as represented by the Minister of National Defence, Ottawa (CA)

(*) Notice: Subject to any disclaimer, the term of this patent is extended or adjusted under 35 U.S.C. 154(b) by 317 days.

(21) Appl. No.: 09/993,488

(22) Filed: Nov. 27, 2001

(65) Prior Publication Data

US 2003/0098421 A1 May 29, 2003

(51) Int. Cl.[7] .............................................. G01N 21/64
(52) U.S. Cl. ................................ 250/458.1; 250/461.2
(58) Field of Search ......................... 250/458.1, 459.1, 250/461.1, 461.2

(56) References Cited

U.S. PATENT DOCUMENTS

| | | |
|---|---|---|
| 3,566,114 A | 2/1971 | Brewer |
| 5,701,012 A | 12/1997 | Ho |
| 5,895,922 A | 4/1999 | Ho |
| 5,999,250 A | 12/1999 | Hairston et al. |
| 6,532,067 B1 * | 3/2003 | Chang et al. ............... 356/318 |

FOREIGN PATENT DOCUMENTS

JP          60-260830          6/1984

OTHER PUBLICATIONS

Today Science Tomorrow Defence "Detection of Biological Warfare Agents" pp. 11–18, Jim Ho.
Biotechnol. Prog., 1991, 7:21–27 "Moritorning Cell Concentration and Activity by Multipty Excitation Fluorometry".
Suffield Memorandum No. 1421 "Detection of BW Agents: Flow cytometry measurement of *Bacillus Subtillis* (BG) Spore Fluorescence", 1993.

Aerosol Science and Technology 4:89–97 (1985) "Performance of a TSI aerodynamic particle sizer", B.T. Chen et al.

Practical Flow Cytometry, Second Edition, 1988, p. 84 "How a flow cytometer works" A.R> Liss, Inc. NY,NY by Shapiro et al.

Schuette et al. "The design and operation of a dual–beam long–focal–length fluorometer for monitoring the oxidative metabolism in vivo" Medical & Biological Engineering vol. 14, No. 2 pp. 235–238, Mar. 1976.

* cited by examiner

Primary Examiner—Constantine Hannaher
Assistant Examiner—Timothy Moran
(74) Attorney, Agent, or Firm—Sean W. Goodwin

(57) ABSTRACT

Apparatus is provided for detection of viable and potentially hazardous biological particles in a population which may be dispersed in fluid flow. The particles are characterized as biological and viable by contacting particles with laser light from a laser diode and then looking for the emission of fluorescence which is typically emitted from bacteria or bacterial spore. Biomolecules which are representative of viability are now known to be excited in range of 320 nm and longer. The resulting apparatus is economical, compact and has low-power requirements enabling portable operation. Preferably, the laser diode is combined with an aerodynamic particle sizer to separate particles for sequential contacts, or with additional timing lasers for establishing particle size.

24 Claims, 20 Drawing Sheets

*Fig. 4*

Fig. 5

FLAPS1 Measurement of BG Aerosol with Nichia Light Source (12 mw) 0.05% BG Slurry Using a Spinning Disk Generator High Resolution Comparison with Reference Data

**Comparison of Three Generations of Detector Technologies
BG Aerosol Generated by Spinning Disk with 0.5% Slurry**

- Flaps1
- Flaps2

Spray On

Nichia laser 13.5 mW
APS Slow Flow Rate

APS Regular Flow Rate

HeCd Laser

APS Slow Flow Rate

*Fig. 6a*

Comparison of Normalised FLAPS1 Fluorescent Data

- Normalised total FL
- Gated % FL

*Fig. 6b*

FLAPS1 Detection of BG Aerosol Using Nichia Laser Diode Field Measurement at CWAL Day 152

Fig. 8

LASER DIODE-EXCITED BIOLOGICAL PARTICLE DETECTION SYSTEM

FIELD OF THE INVENTION

The present invention is related to process and apparatus for detecting the presence of biological agents utilizing stimulation and detection of fluorescence therefrom.

BACKGROUND OF THE INVENTION

There is a recognized need for the detection of undesirable concentrations of potentially harmful airborne bacteria in health care environments, laboratories and in warfare conditions. To date, equipment used for such purposes have been unreliable and expensive to build and operate. Further, the associated support requirements have been very high, both in power requirements and maintenance. Accordingly, to date, their use has been restricted to industrial and governmental use. The service industry or the homeowner, concerned about residential and environmental monitoring, has not had practical access to such equipment.

Biological aerosols, mostly harmless, are indigenous to many environments, including homes. Microorganisms are naturally aerosolized in the atmosphere, often becoming a biological burden to downwind communities. For example, municipal wastewater aeration tanks can produce coliform bacteria, and washing of dairy processing plants can produce a persistent biological aerosol. In the hog industry, diffusion modeling has shown that aerosolized microorganisms could spread infection over a 150 $km^2$ area among swine herds. Indoor microbiological air quality in homes and offices has demonstrated the prevalence of bacteria and fungi, for example bacterial numbers can range upwards to 800 viable particles/$m^3$ in homes and up to 500 in offices. Typical values of fungi are about half as abundant. Fairly similar findings have bee reported as recently as 1998 by the US Environment Protection Agency which has recently taken an interest in measuring indoor and outdoor bio-logical aerosol quality.

Processes for the detection of airborne particles typically comprise sizing and characterizing the particles as biological. Such characterization of particles as being biological can accomplished by detecting a specific biomolecule present only in bio-viable particles. Most living cells contain a coenzyme or biomolecule, nicotinamide adenine dinucleotide phosphate (NADP). NADP is a biomolecule which is essential for cellular metabolism as an electron or hydrogen acceptor and is therefore an essential constituent in most biological processes to be viable. NADP is the oxidized form of NAD(P)H or nicotinamide adenine dinucleotide hydrogen (NADH). It is known that NADH can be excited with ultraviolet light and will fluoresce. The fluorescence excitation and emission wavelengths of NADH are well separated, which facilitates detection. The excitation wavelength of NADH is centered at 340 nm in the near ultraviolet spectrum, and its fluorescent emission wavelength extends from 400 to 540 nm.

Apparatus are known for implementing excitation and detection of fluorescence of NADP in discrete particles. A fluorescent aerodynamic particle sizing (FLAPS) apparatus is disclosed in U.S. Pat. Nos. 5,701,012 and 5,895,922 issued to Dr. J. Ho, the entirety of both patents being included herein by reference. The Dr. Ho disclosed the use of HeCd and tripled frequency YAG lasers, which emit a laser light beams having a wavelength in the range of 340–360 nm, ideal for the excitation of NADH. Additional aspects addressed by Dr. Ho include combining the laser excitation and detection technology with an aerodynamic particle sizer which implements converging airstreams for separating particles for analysis. Accordingly, the FLAPS apparatus comprises an aerodynamic particle sizer, the ultraviolet laser and a photomultiplier tube (PMT) for detecting fluorescence from particles. Focusing optics direct the laser to contact each passing particle. A further aspect addressed by Dr. Ho was to implement sequential lasers across the particle's path for establishing the speed of the particle in the separating airstream, resulting in enhanced correlation with biological viability.

The lasers used in the prior art FLAPS apparatus add significantly to its complexity. For instance, the 100 cm long, 30 mW, cooled 325 nm Helium-Cadmium (HeCd) laser and focusing optics are large, heavy, and power intensive. The disclosed system weighs in at about 90 kg and consumes 800 watts of electrical power. The HeCd laser, power supply, and the particle sizing 633 nm HeNe lasers are all mounted to a 60 by 150 centimeter optics table and enclosed with a sheet metal cover to give the system a height of about 30 cm. In order to operate this apparatus remote from an industrial site requires the addition of a power generator and a technician to ensure minimal interruption between failures.

To date, the FLAPS apparatus has been limited to the use of an expensive, and unreliable, light sources such as the conventional HeCd or YAG lasers described above to provide the wavelengths suitable to excite NADH for signaling the detection of viable biomolecules and which was known to be suitable also to detect NADH even in spores.

The above prior references identify and set forth the concerns about the detection of certain hard-to-assess biological particles such as anthrax, particularly in the spore form. Questions were resolved, whether there was sufficient intrinsically fluorescing biological matter (NADH) to enable one to establish whether the particle was viable (biologically alive), and thus potentially hazardous. The 30 mW HeCd laser disclosed in the FLAPS apparatus was deemed successful for stimulating measurable fluorescence of NADH from spores.

However, as stated, the HeCd laser is expensive, unreliable and requires laser cooling and a significant power source. This severely limits its usability in critically hazardous, mobile and portable operations.

There was therefore a demonstrated need for a more practical, more portable and economical approach to biomoloecule detection. In improving the apparatus by applying a new type of laser, the applicant introduced significant uncertainly in its ability to reliably distinguish viable from non-viable particles. The laser has different operating properties and characteristics including its power output and its light wavelength; either of which could limit the apparatus's ability to detect viable particles. This task ultimately required significant effort and expense to overcome the specific uncertainty about the ability of such improvements to provide reliable and repeatable results.

SUMMARY OF THE INVENTION

Apparatus is provided for identifying viable biomolecules in a stream. The apparatus is an improvement over related instruments, the advantages including achievement of substantial reductions in cost and power consumption which enables widening application of the technology from large industrial, governmental and military applications to also include smaller commercial and residential use. Implementation of the concepts described herein have expanded our knowledge into heretofore unknown response of biomolecules other than NADH. In the course of improving detection apparatus, the applicant has also discovered that a new range of biomolecules can be used which are indicative of particle bio-viability. Further, in expanding this range, new apparatus having improved economies and efficiencies have also been discovered while disadvantages including complexity and high power demands of the prior art apparatus are avoided.

Figure 17A:
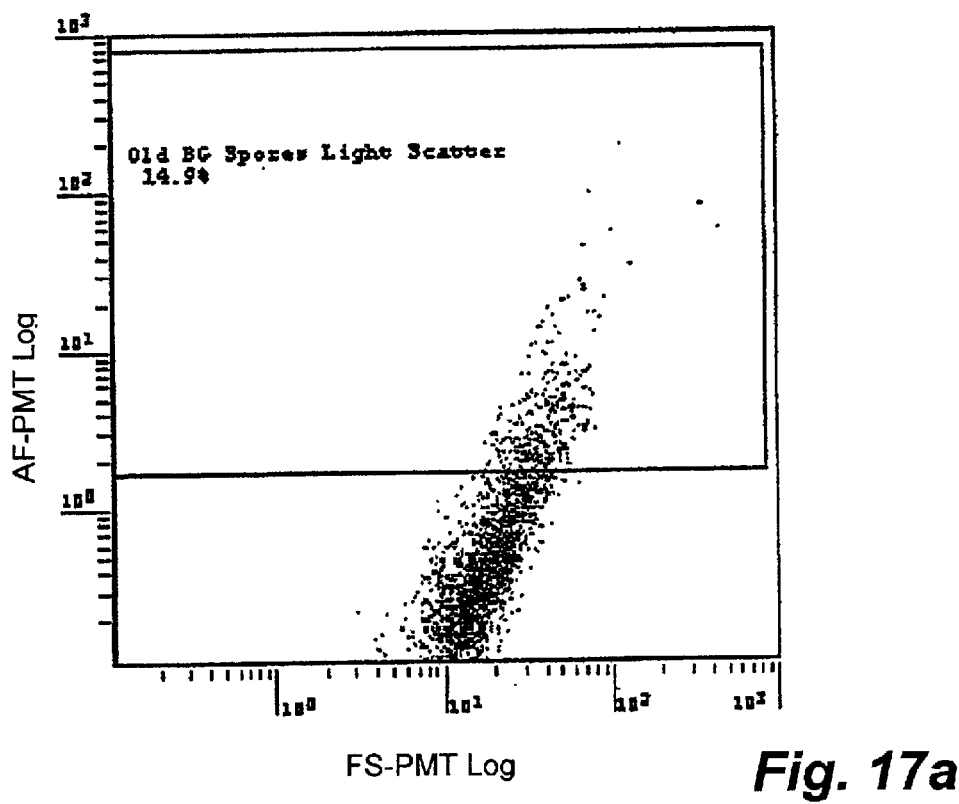
Figure 17B:
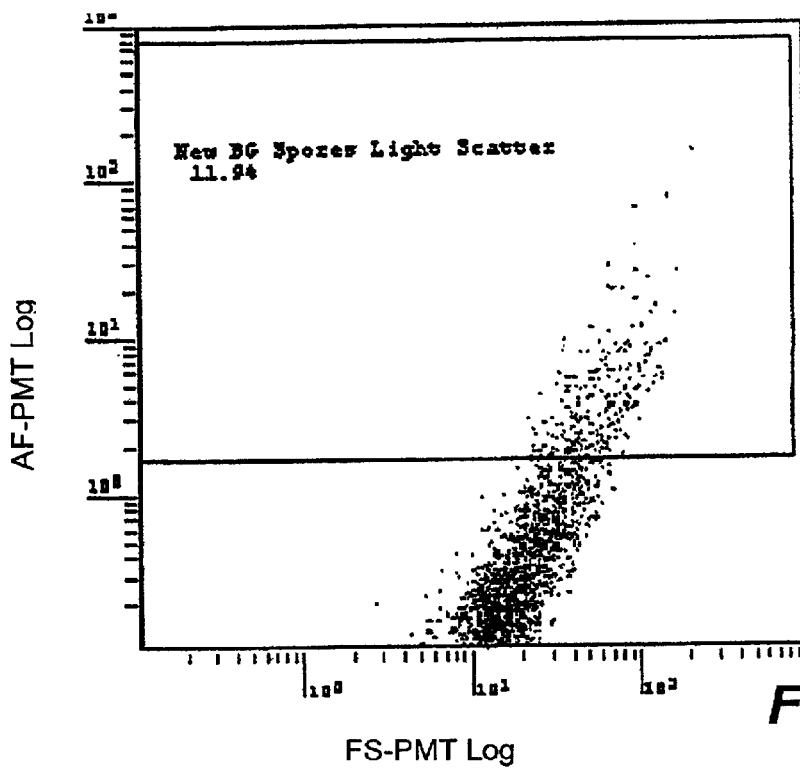

Simply, in a preferred aspect, a laser diode is provided and applied as the excitation source. To date, laser diodes are not available at the wavelengths known to be most suited to excite the known reactive biomolecule NADH; however, they are currently available at slightly longer wavelengths. Heretofore, it has not been confirmed, whether biomolecules indicative of bio-viability exist (other than NADH) which provide similar fluorescence characteristics under laser light at other wavelengths or which are discernable at lower light emission power. It had not been confirmed whether biomolecules such as flavinoids, believed to be excited at wavelengths longer than that used to excite NADH, are even present at all in hazardous particles like spores, or are even available in sufficient quantities to be excited by laser light. Neither has it been determined that such longer wavelengths would even be suitable for exciting any biomolecules, such as flavinoids, so as to produce measurable fluorescence.

Surprisingly, applicant has determined that viable particles, including spores, can be excited to fluoresce using a laser diode operating with power output and power requirements as low as about 8–15 mWatts. Conventional apparatus using a shorter wavelength He—Cd laser may also operate at relatively low power output levels, such as about 30 mW, however the practical and overall power requirements to operate the laser are many orders of magnitude greater (say 800 Watts) when the operation of necessary ancillary equipment such as laser cooling systems are included. Further, diode lasers are distinguished from conventional gas or solid state lasers by their ability to be pumped directly by an electrical current which results in efficient operation, approaching power conversion efficiencies of 50%. The gas and solid state lasers, which generally pumped by plasma excitations or an incoherent optical flash lamp source respectively, exhibit efficiencies which are more in the order of 1%. Another difference between diode and other lasers is their physical size; wherein gas and diode pumped solid state lasers are typically tens of centimeters in length, laser diode assemblies are generally about the size of the grain of salt and are only bulked up slightly (to about one centimeter) mostly for the purpose of handling and mounting purposes.

Therefore, in a broad aspect of the invention an improved apparatus is provided for identifying the existence of biologically viable particles within a particle population containing a mixture of biologically viable and biologically inert particles. The improved apparatus comprises: a solid state excitation source wherein said source is a laser diode for emitting a light beam being directed to contact particles of the particle population and having a wavelength from about 320 nm to 500 nm which is operative to excite biomolecules contained therein to produce fluorescence; a photon counter for measuring the intensity of fluorescence emitted from each contacted particle and producing a signal indicative thereof; and a microprocessor for comparing each contacted particle's fluorescent intensity signal against predetermined criteria and establishing whether that particle is a biologically viable particle or an inert particle.

Preferably, the improvement is applied in combination with particle discretization or segregation apparatus and more preferably in combination with particle sizing apparatus for improving the identification of the biomolecules as respirable and hazardous.

BRIEF DESCRIPTION OF THE DRAWINGS

FIG. 1 is a graph depicting the excitation and emission wavelengths for NADH and Riboflavin;

FIG. 2 is a plot of a laser diode optical alignment calibration using fluorescent latex beads for illustrating a good tight distribution of fluorescence brightness, as a function of intensity channel, versus number population.

FIG. 3 is a graph of total fluorescence particles detected using the laser diode and HeCd lasers sequentially at slow, regular and slow APS flow rates; the results illustrating substantially continuous and comparable detection results regardless of the excitation light source;

FIG. 4 is a graph illustrating the good correlation of fluorescent particle measurement by the laser diode with live particles as determined with colonies grown on agar plates, and as sampled from the same aerosol source;

FIG. 5 is a graph according to a portion FIG. 4, and having an expanded time scale for the narrow 4 minute window in which the agar plates were sampled; the arrows illustrating points of coincidence;

FIG. 6*a*, a graph is presented which illustrates the FLAPS2 frequency-tripled, pulsed, solid state YAG laser technology versus the FLAPS1 switched sequentially between use of Nichia 402 nm laser diode and the HeCd laser through a test of introduction of BG spores, slow and regular APS flow rates;

FIG. 6*b* is a graph of the data of FIG. 6*a* normalized by a factor of 1.567 for slow flow rates;

FIG. 7 is a graph of a Spearman rank order, non-parametric correlation of the data of FIG. 6*a* illustrating a good correlation coefficient of 0.86;

FIG. 8 is a graph of a field measurement test of the laser diode, the results of which are favorably coincidence with viable counts determined per agar plates;

FIGS. 9 and 10 are graphs of another field and comparative measurement test of the 402 nm and the HeCd lasers respectively, both at low aerosol concentrations while still producing favorably coincidence with viable counts per agar plates, and at levels above noise;

FIG. 11 is a graph which illustrates the laser diode and HeCd laser's sensitivity respectively to background aerosol material;

FIGS. 12 and 13 are graphs which illustrate the performance and capability of the laser diode to sense ovalbumin which was released 200 m upwind of the instrument and the capability of the HeCd laser to sense ovalbumin released 100 m upwind of the instrument respectively, and in each case several events met an alarm threshold when bioparticles were distinguished over background;

FIGS. 14*a* and 14*b* relate to tests performed with a 413 nm ion laser of Example 8, and illustrate plots of negative population calibrations of the AF-PMT presented as AF-PMT vs. FS-PMT and AF-PMT intensity;

FIGS. 15*a* and 15*b* are plots of positive population calibrations of the AF-PMT presented as AF-PMT vs. FS-PMT and AF-PMT intensity;

FIGS. 16*a* through 16*g* are histograms of FS-PMT log versus AF-PMT log for the 413 nm ion laser at sequentially decreasing power settings of 50, 40, 30, 20, 15, 10 and 5 mW respectively; and FIGS. 17a and 17b are comparative plots of the HeCd laser on old and new spores respectively, demonstrating performance which is similar to the 413 nm ion laser in the specific environment of the flow cytometer.

DETAILED DESCRIPTION OF THE PREFERRED EMBODIMENT

An instrument is provided comprising means for contacting substantially discrete particles of a particle population with an excitation light source, wherein said light source being a laser diode. As set forth in a series of examples, the laser diode has been found to emits a wavelength which is suitable for exciting biomolecules in the contacted particles. While it is anticipated that the laser diode would be implemented as the sole excitation light source in a new instrument, for the purposes of this discussion and as set forthin the examples, a laser diode was conveniently retrofit into an existing prior art FLAPS apparatus so as alternately apply a conventional laser light source or to apply a laser diode source according to the present invention.

As described below, a laser diode emitting a light beam has been tested with particles flowing through a conventional aerodynamic particle sizing (APS) apparatus for a series of Examples 1–7 and also through a flow cytometer in Example 8.

Generally, the instrument provides an environment for contacting subject particles of a population with an excitation laser beam. The prior art FLAPS apparatus is such a platform suitable for implementing the present invention. A nozzle is provided for accelerating an airstream containing particles for discharge past a pair of laser beams. Timing of the particle's flight between laser beams enables determination of the particle's velocity and size. The arrangement of this portion of the apparatus is consistent with the conventional APS instrument. The particles then traverses a laser beam for fluorescence characterization of the particle to determine biological viability. The details of the APS apparatus and principles of fluorescence characterization are set forth in detail in U.S. Pat. No. 5,701,012 to Dr. J. Ho, the entirety of which is included herein by reference. This apparatus utilizes a HeCd laser and is referred to herein as FLAPS1.

A further improved prior art apparatus is disclosed in U.S. Pat. No. 5,895,922 to Dr. J. Ho, the entirety of which is included herein by reference, and which discloses a diode-pumped Nd:YLF laser frequency-tripled laser, the system being termed FLAPS2.

The FLAPS2 apparatus further provides a pair of spaced laser beams for detection of a particle's flight time and size. The excitation laser can be pulsed to provide selective firing and thus only excite particles matching desired size characteristics. This feature offers a "smart" technique for interrogating the biological characteristics of a single particle and also avoids unnecessary firing of the laser at background material of less than 1 μm in size.

Limited by their lasers, both FLAPS1 and FLAPS 2 employ an excitation frequency of between about 325 and 349 nm.

Turning to the present invention, a laser diode replaces the cooled HeCd laser of the FLAPS1 apparatus. Laser diodes are solid state excitation sources which are small, inexpensive, emit longer wavelengths than the prior FLAPS apparatus and typically have low power consumption and output. Low cost visible light laser diodes and their driver circuitry are typically packaged and used in handheld laser pointers and are button-battery powered. There is no need for expensive and bulky cooling systems. To Applicant's knowledge, it has not been suggested to date that this technology is adaptable to biomolecule detection, in part due to the availability being limited to longer light wavelengths and their low power output. It was particularly uncertain whether laser diodes could be adapted to the detection of biological spores, such as anthrax spores, which present a serious airborne threat.

While other apparatus could be applied to contact particles and an excitation source, a convenient apparatus was available in the FLAPS2 apparatus described in U.S. Pat. No. 5,895,922, the base instrument comprising an APS having a tubular nozzle and an airstream containing particles, which may or may not be biological, and may or may not be viable. The APS acts as a sequencer, directing the particles to exit the nozzle in a sequential manner, traveling downwardly along a linear flight path and traverse two path-intersecting laser beams. Preferably, two laser beams are used for particle detection and time-of-flight determination. The position of each particle in the airstream is determined as a function of time and the particle's time of flight is measured between two points along a flight linear path so as to establish the particle's size For the purposes of the present invention, the apparatus supporting the 340–360 nm HeCd laser of FLAPS1, its power supply and optics were retrofitted with a laser diode emitting a nominal 402–405 nm laser beam. For comparison purposes, the FLAPS1 apparatus was modified to enable alternate use of either the HeCd or the laser diode.

A suitable laser diode is a Nichia light source which emits at about 402 nm. Such a light source is a Nichia laser diode, model number NLHV500A (nominal 8 mW) by Nichia Corporation, Tokushima, JAPAN. A similar wavelength (405 nm), higher power diode is the 30 mW model NLHV3000E. Other laser diodes are available from the same manufacturer which range in output from 400 to about 450 nm, with others being developed. Common laser pointers utilize diodes capable of wavelengths typically in the range of 645–680 nm.

The excitation source is positioned just below the nozzle and below the APS laser beams. Laser beam output is aligned by a collimating lens. A suitable lens is a model 307-4606-670, 4.6 mm focal length, numerical aperture 0.53 available from Optima Precision, Inc., West Linn, Oreg.

The particles are preferably first sized to determine respirability. The particles are then excited by either the HeCd or the laser diode laser beam and the particles are then monitored for fluorescent emission from biomolecules which is characteristic of viable bioparticles. Fluorescence is detected using a using a photon counter such as a PMT. As set forth in the Ho patents, a microprocessor compared each contacted particle's fluorescent intensity signal against predetermined criteria for establishing whether that particle is a biologically viable particle or an inert particle.

Figure 1:
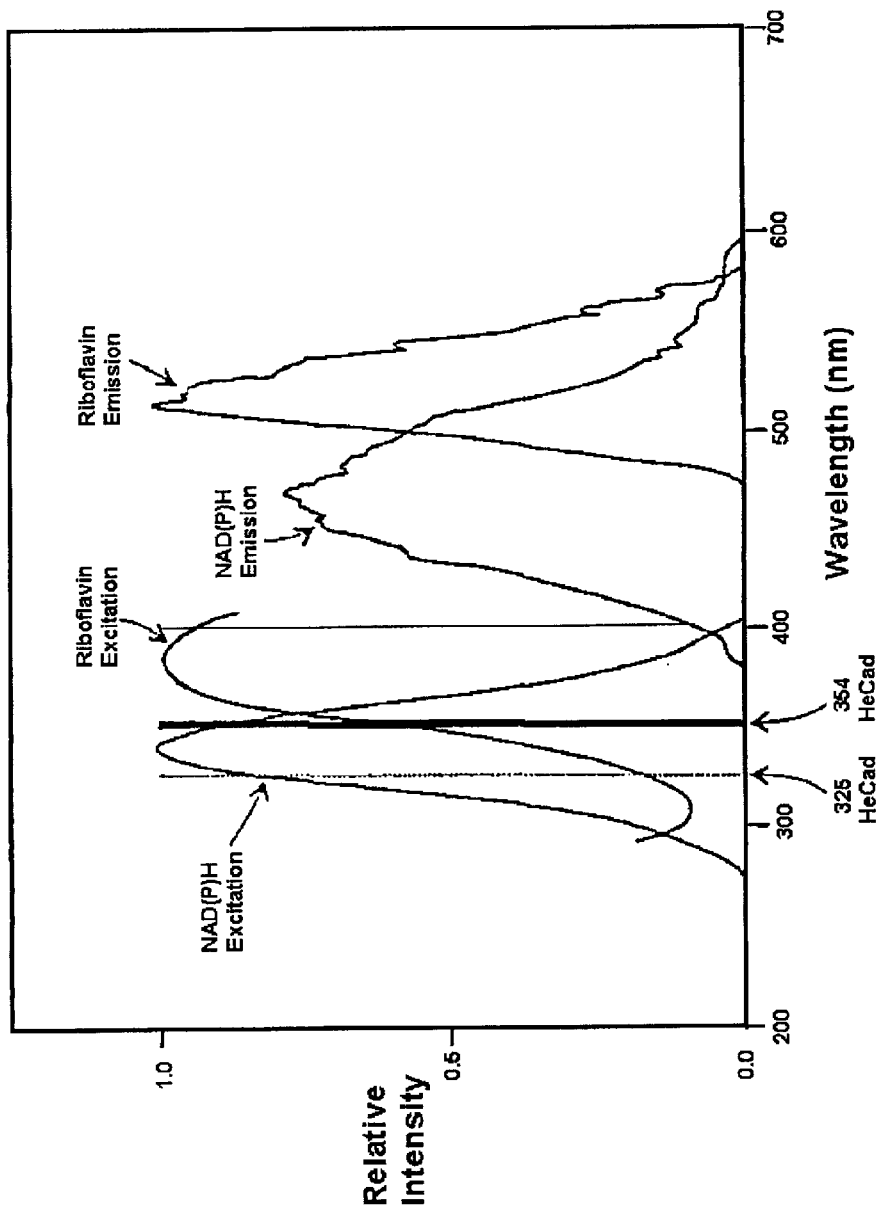

As shown in FIG. 1, the known biomolecule NAD(P)H exhibits peak excitation at wavelengths of approximately 325 nm–354 nm with characteristic emission between 420 nm and 560 nm and with a peak at approximately 460 nm. Riboflavin, on the other hand, exhibits peak excitation at approximately 400 nm, with characteristic emission between 475 nm and 580 nm. Whether riboflavin exists in biomolecules had not been determined. This data represents material published by Li et al. in *Monitoring Cell Concentration and Activity by Multiple Excitation Fluorometry*, Biotechnol. Prog., 1991, p:21–27. The prior art system using the HeCd laser was designed to illuminate the particles at 325 nm and detect fluorescence in the region from 420 nm to 560 nm.

The present system, using the Nichia laser diode, was applied to ascertain if the low power, higher frequency laser diode could excite particles at 402 nm and detect fluorescence as effectively as the higher power, complex and expensive HeCd laser implementation. Heretofore, applicant was unaware of research which confirmed the presence of riboflavin in the nearly inert spore form. Solovieva et al (Solovieva, I. M., R. A. Kreneva, D. J. Leak and D. A. Perumov. 1999. *The ribR gene encodes a monofunctional riboflavin kinase which is involved in regulation of the Bacillus subtilis riboflavin operon.* MICROBIOLOGY-UK, 145: 67–73.), however, reported isolation of the *Bacillus subtilis* DNA that contained the riboflavin operon and was able to clone the operon into *E. coli*, suggesting the ability of *Bacillus subtilis* to synthesize riboflavin. It was uncertain as to whether levels, if present, were sufficient to allow detection.

The following examples illustrate the surprising ability of the economical low power, longer wavelength laser diode to successfully excite and fluoresce some form of biomolecule, other than the known NADH, in viable particles. The applicant hypothesizes that one of the biomolecules which is fluorescing at these longer wavelengths is riboflavin.

EXAMPLES

Unless otherwise stated for each individual example, the following equipment and conditions were used for comparing the performance of prior art: FLAPS1 using the HeCd laser, the prior art FLAPS2 using a pulsed solid state Nd:YLF laser, and the FLAPS1 particle apparatus in combination with the present invention's laser diode. Tests were conducted to determine whether biologically viable particles could be distinguished from a particle population containing a mixture of biologically viable and biologically inert particles.

As suggested above, for comparative experimentation purposes only, a FLAPS1 instrument was constructed having both a HeCd laser and a Nichia laser diode installed for ease of comparison of the individual results of excitation. In incorporating both prior art gas laser and diode lasers into the same instrument, it became necessary to prevent the excitation light from interfering with the fluorescence detector. Therefore, a corresponding long pass filter, having a cut off at 435 nm, was provided in addition to other existing filters for the FLAPS1 when the Nichia laser diode was used. Such a filter is a Schott Glass GG 435, available from Melles Griot, Irvine, Calif. The GG435 filter was placed between the primary light collection lens and the dichroic filter.

To enable alternate selection of the light sources in the following experiments, a steering mirror on a Kinematic mirror mount was inserted along the exciting beam path. Such a mirror and Kinematic mount are a 02 MFG 015/038 mirror available from Melles Griot, Irvine, Calif. and a BKL-4 mount available from Newport Corporation, Irvine, Calif.

The laser diode was operated in constant current mode, with a power readout connected to the laser's internal photodiode. The power tended to droop as the laser warmed over the course of each trial. Accordingly, during initial startups, manual adjustments were made to maintain laser diode output power between 12 and 14 mW. It was noted that power droop and compensating manual adjustments could affect data displays as slight distortions in the fluorescence intensity data.

In the case of the FLAPS2 apparatus, to compensate for higher than optimal pulse energy, an optical density filter was used to pass only 10% of the laser beam output to contact the particle. This resulted in lower background noise and better signal-to-noise characteristics. The laser was triggered when a particle was detected with a minimum time between triggers of 200 $\mu$sec. To compensate for different particle flight times due to particle size, a "skeet shooting" look-up table was used to synchronize laser trigger times. The table provided information that relates particle size to time delay for firing the laser. Accordingly, through firmware commands, selective firing could be exercised to excite only particles of desired size characteristics, avoiding unnecessary firing to contact mere background particles.

During real time sampling, the instrument presents size and fluorescence intensity information for each contacted particle. Data derived from a sampling period, typically 3 seconds, can be reduced to a fractional number (gated % fluorescent); this represents the percent of particles that exhibited fluorescent signal above a preset size and intensity threshold. A threshold level can be determined for each environmental condition by observing the prevailing background conditions. An alternate method to present fluorescence data is to derive a "signal-to-noise" ratio. This is done by comparing the mean of background gated % fluorescent with new "unknown" or "biological" data.

Note that a prototype aerosol concentrator (model XMX, SCP Engineering, St. Paul, Minn.) was used as a front end to the FLAPS2 intake to enrich the population of background fluorescent particles for better statistical counting. The concentrator was optimized to minimize size, weight and power consumption; operating at 400 liter/min and concentrating to 1 liter/min delivered to the FLAPS2 intake. Improved particle throughput provided by this setup facilitated a rapid sampling time of 3 seconds. In practice, an additional 1 second penalty was incurred for computational and data handling overhead. By this protocol, aerosol data could be collected continuously every 4 seconds over long periods unattended by the operator.

The instrument was calibrated for use at a wavelength of 402 nm using an aerosol of fluorescent latex beads (catalog number B0200, Duke Scientific Corporation, Palo Alto, Calif.). The latex beads exhibit a blue fluorescent dye having three excitation peaks: 365 nm, 388 nm, and 412 nm. The 365 nm and 388 nm excitation emit at a peak at 445 nm and the 412 nm excitation emit at a peak of 445 nm, with a secondary emission peak at 473 nm. As 402 nm wavelength falls on the sides of both the 388 nm and 412 nm excitation peaks, the result is a combination of the 445 nm and 473 nm emission peaks. The latex beads were aerosolized using a TSI Model 3076 nebulizer, together with a TSI 3074B air supply filter and a TSI 3012 aerosol neutralizer.

Biological aerosol dissemination of *Bacillus subtilis* var niger spores (BG spores) was accomplished with a Hudson nebulizer (Model 1700, Hudson Oxygen Therapy Sales Co., Wadsworth, Ohio) at 172–206 kPa (25–30 psi). A suspension containing BG spores in the range of 5 to 30 $\mu$g plus 4 mg silica gel (Syloid 245, Davison Chemical, Baltimore, Md.) per ml was used as the starting material.

Field biological aerosol dissemination of BG spores took place about 100 m to 250 m upwind of the detection system. Culturable particles were impacted into an agar plate and grown to determine the presence of live content.

Egg albumin powder (A5253) used as a protein-based toxin simulant, was obtained from Sigma Chemical Co. An aerosol was produced by a Nordson Tribomatic® 500 spray gun (Canwest Pumping Systems Ltd. Calgary, Alberta Canada).

A correlation analysis was performed to estimate the degree to which FLAPS measurements vary together with live reference data and the common cause is the presence of live biological aerosols. The data was tested for distribution normality using non-parametric methods In the following Examples 1–6, a nominal 402–405 nm laser diode was used to confirm the detection of biomolecules. In Example 8, recognizing that that BG spores may also be sensitive to even longer wavelengths, a further conventional ion laser was also applied, specifically at 413 nm.

Example 1

Figure 2:
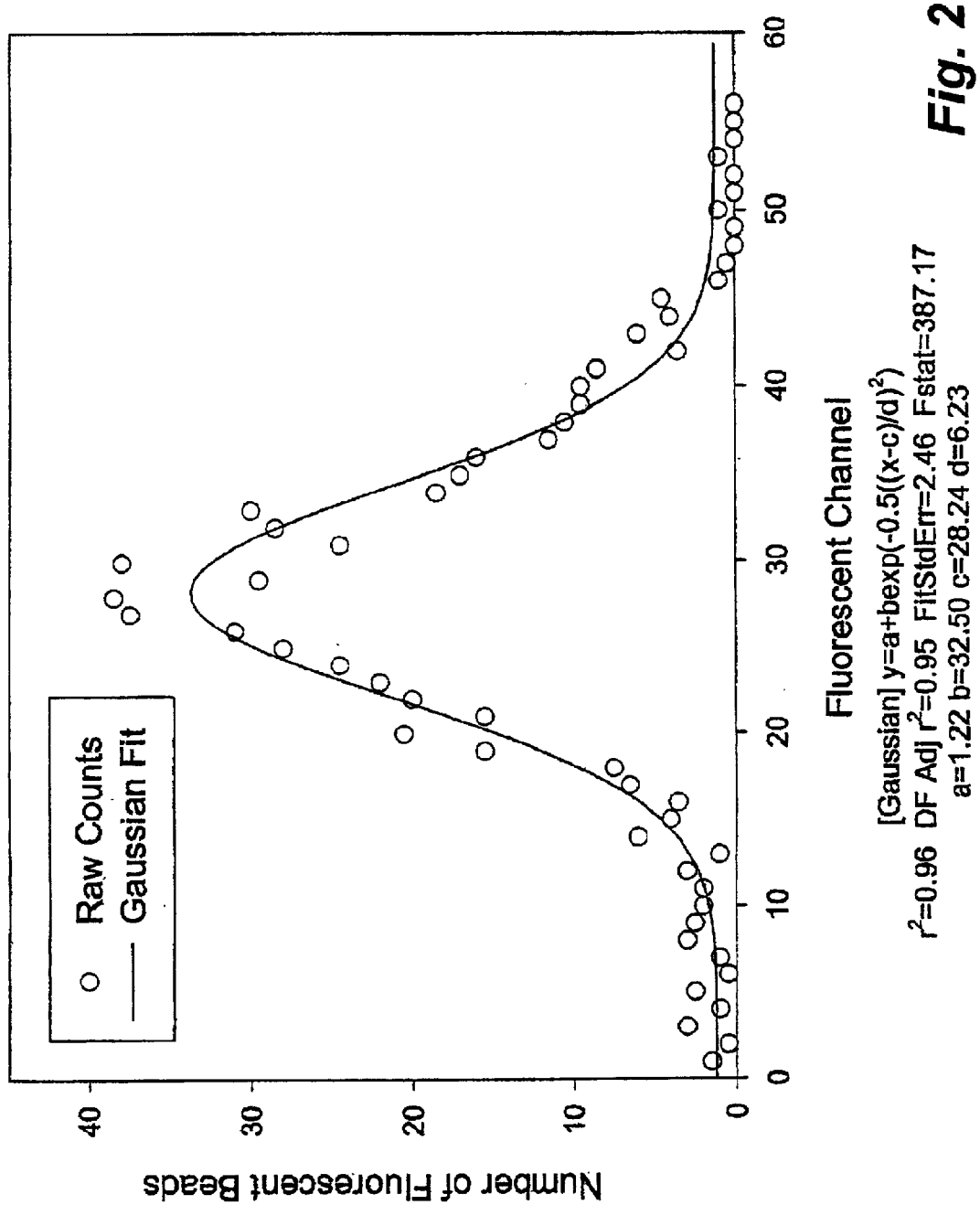

As a calibration check for good optical alignment, standard fluorescent latex beads were examined with FLAPS1 using the Nichia laser diode light source. Having reference to FIG. 2, the data is seen to conform well to a Gaussian distribution, with a fit correlation coefficient of 0.96. As measured by the size distribution capability of the instrument, 2 $\mu$m beads were occupying 2 size channels, indicating tight banding of the sizing function. The conclusion was that the optical components were properly installed and optimized for fluorescent detection of particulate aerosols.

Example 2

Figure 3:
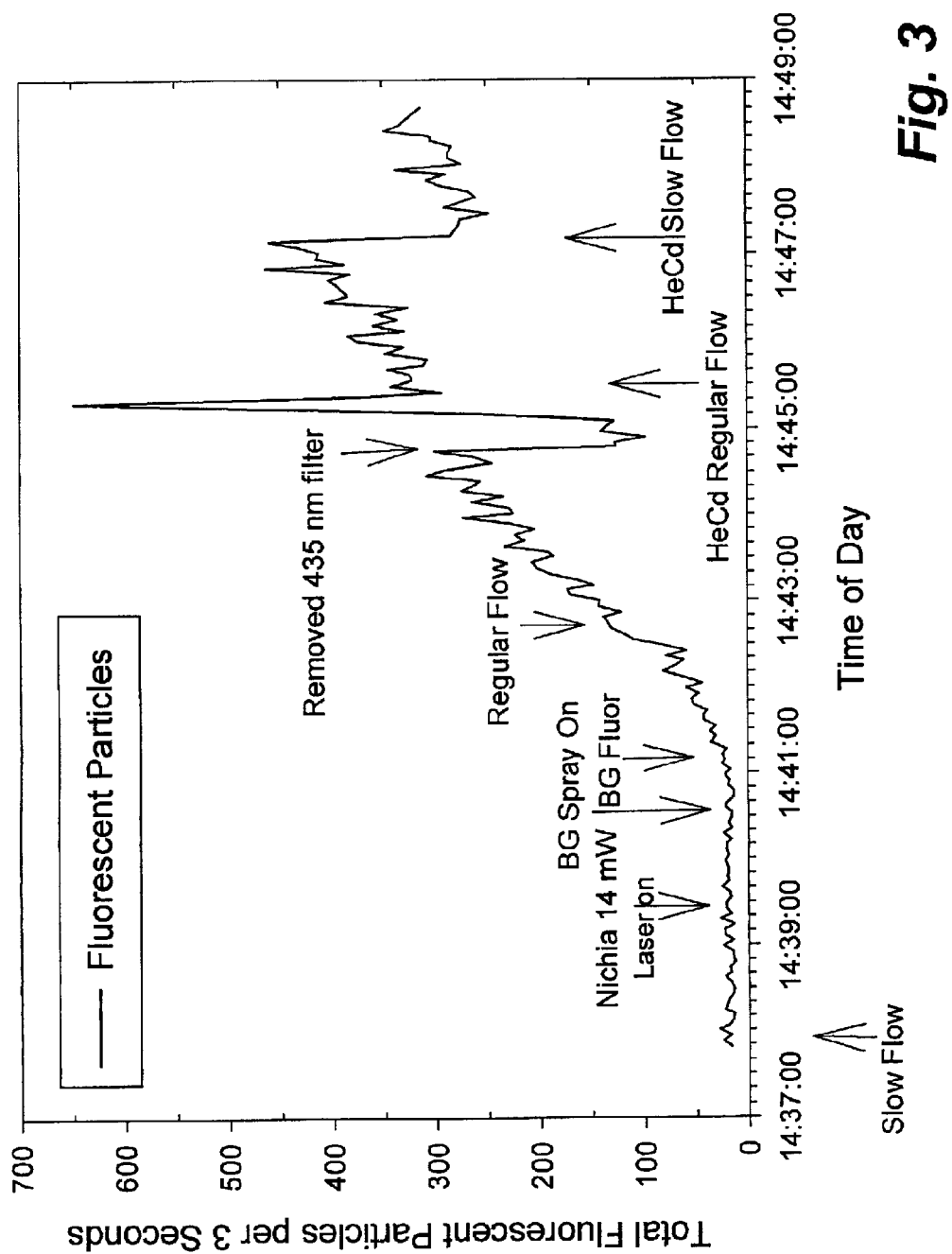

As shown in FIG. 3, background measurements were performed in the FLAPS1 particle chamber followed by the gradual introduction of a spore aerosol (BG). The experiment was started with a slow sample flow rate to improve the signal to noise measurement due to slower particle transit time in the laser diode beam. Fluorescence signals remained relatively constant even when the Nichia laser was turned on (see time 14:39:25) suggesting that HEPA filtered air in the chamber contained little, if any, background material that had fluorescence characteristics. The aerosol spray of biological aerosols was introduced at 14:40:32 and shortly thereafter, at 14:41:13, the first visible BG fluorescence was measured.

Sample flow rate was increased to a regular flow rate at 14:42:37, resulting in some slight effect on the rate of detection, as observed from the slope of the trace. The measurement rate continued to rise until at 14:44:30 when the 435 nm filter was removed in preparation for changing from the Nichia laser to the HeCd laser. A dip in the measurement can be observed as the laser was changed (14:45:00). Following a switch to the HeCd laser, the data resumed a similar rate of increase as had been observed with the Nichia laser. Moreover, when the flow rate was attenuated to the same slower level as applied at the beginning of the experiment, the fluorescent particle sampling rate appeared to drop significantly, similar to the measurements at the start of the test.

Example 3

Figure 4:
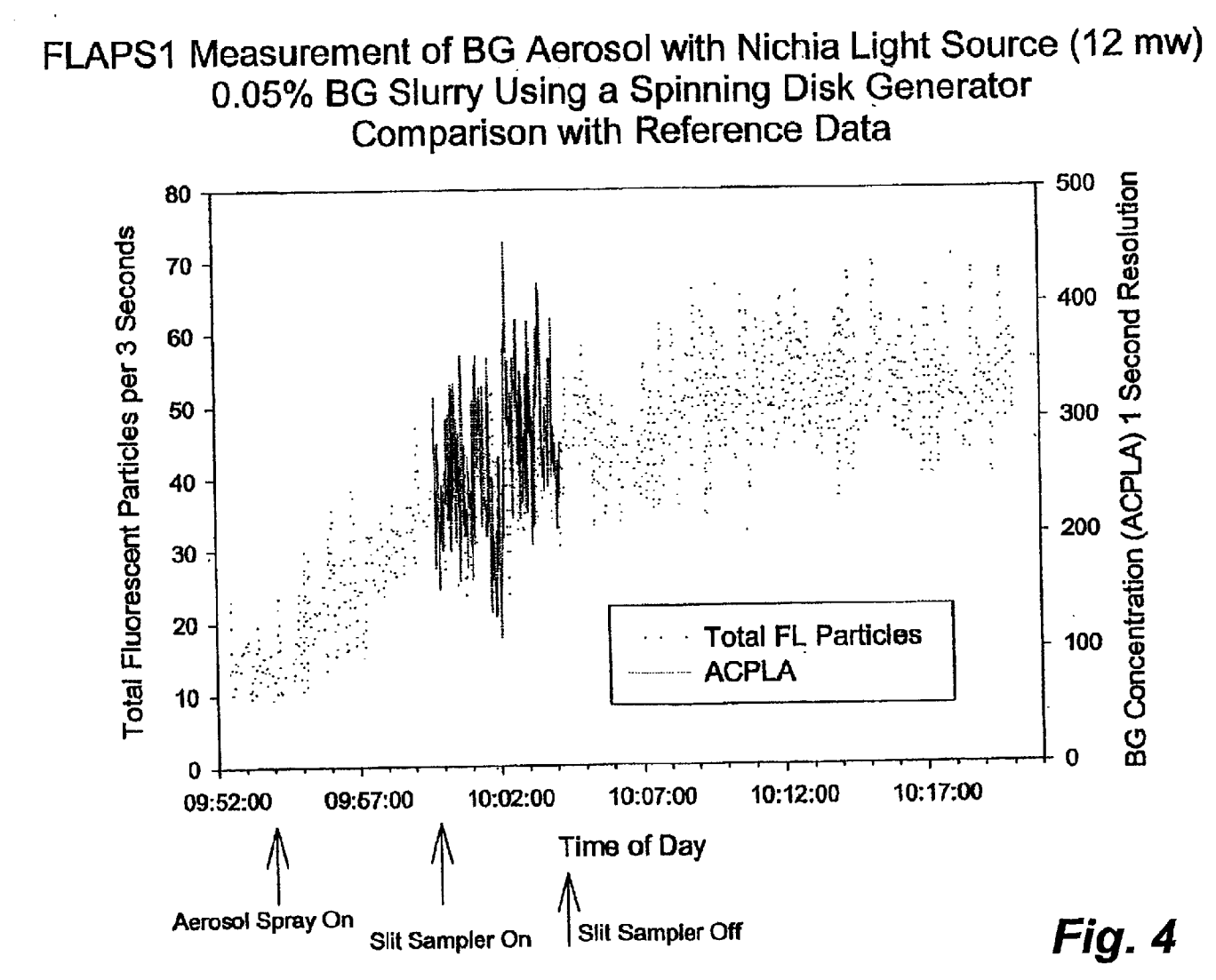

Having reference to FIG. 4, in another BG aerosol chamber test using the FLAPS1 particle chamber, the fluorescent particle measurement was correlated for a 4 minute collection span with colony-forming live particles. Slit sampling was performed to capture live particles in high resolution with respect to time, to resolve particulate material in 1 second time slices, over a 4 minute time span. The aerosol generator was a spinning disk device designed to produce relatively high concentration of particles. The results of the live particles were expressed as Agent Containing Particles per Liter of Air (ACPLA).

The rate of increase of fluorescence using the Nichia laser, roughly paralleled that of the live particles.

The same reference data is shown in FIG. 5, expanding the 4 minute collection span so as to better inspect and compare the dynamics of the two measurement methodologies, the laser method being instantaneous, the agar plate method being long term (and clearly ineffective to warn of a biological threat). The arrows in FIG. 5 provide subjective and favorable indications as to when the two data sets appear to coincide.

Example 4

A FLAPS2 instrument powered by a frequency-tripled Nd:YAG light source was used to measure BG aerosol simultaneously with the experimental FLAPS1 instrument equipped with interchangeable Nichia laser diode and the HeCd laser light sources. A similar experimental approach as used in Example 3, was used to supply a dynamic BG aerosol concentration in a chamber while optical measurements were recorded. The response of the two FLAPS instruments was compared.

As shown in FIG. 6a, the Nichia laser diode was selected in FLAPS1 and the aerosol generator was run at a slow flow rate at the beginning of the test. Shortly after the aerosol spray started, both FLAPS1 and FLAPS2 detectors measured the presence of fluorescent particles. The absolute counts were dissimilar, as the FLAPS2 was a pulsed device, providing a more energetic excitation for each contacted particle, resulting in emission signals from small or dim particles. No attempts were made to detune the FLAPS 2 light source.

FLAPS1 was switched to run on a regular sampling flow rate at 11:24:00 and again using the Nichia laser diode. The two FLAPS apparatus registered roughly similar particle sampling rates. FLAPS1 was then switched to the HeCd laser at about the same time the aerosol was stopped. Subsequent HeCd data roughly paralleled the decreasing fluorescence measured by FLAPS2.

Throughout the testing, all three lasers induced fluorescent signals that reflected the dynamic presence of BG spore particles in the chamber.

Having reference again to FIG. 6a, FLAPS1 data appears disjointed due to switching between slow and regular flow rates giving the appearance of slightly different particle counts rates under each flow regime. In contrast, the FLAPS2 curve is a smooth trace disrupted only by time gaps reflecting changes in experimental conditions. Mathematically, compensation was attempted for the different flow rate by normalizing the particle counts. In FIG. 6b, slow flow values were adjusted by a factor of 1.567 to account for the flow differential.

Further, FLAPS data can be presented as a fraction of particles greater than a particle size cut, expressed as percentage of total particles measured. This better reflects biological content in environmental conditions where absolute particles may fluctuate over time but the size distribution is expected to remain fairly constant in the absence of unnatural disturbances.

Referring to FIG. 6b, data is plotted as gated % fluorescence, illustrating a different dynamic expression of the aerosol conditions in the chamber. The gated fraction represents particles >2 μm as a percentage of the total particles at a given time, measuring spore aggregates rather than individuals. Further, the gated % fluorescent value prior to the aerosol was highly variable, due to low count statistics. A dramatic increase in the gated fraction was observed once the aerosol was started. The drop in this value over extended time reflects changes in particle size dynamics. For example, the larger population may have been reduced due to falling out more rapidly with respect to the smaller particles. The restoration to regular flow also affected the population balance of the larger size fraction.

Figure 7:
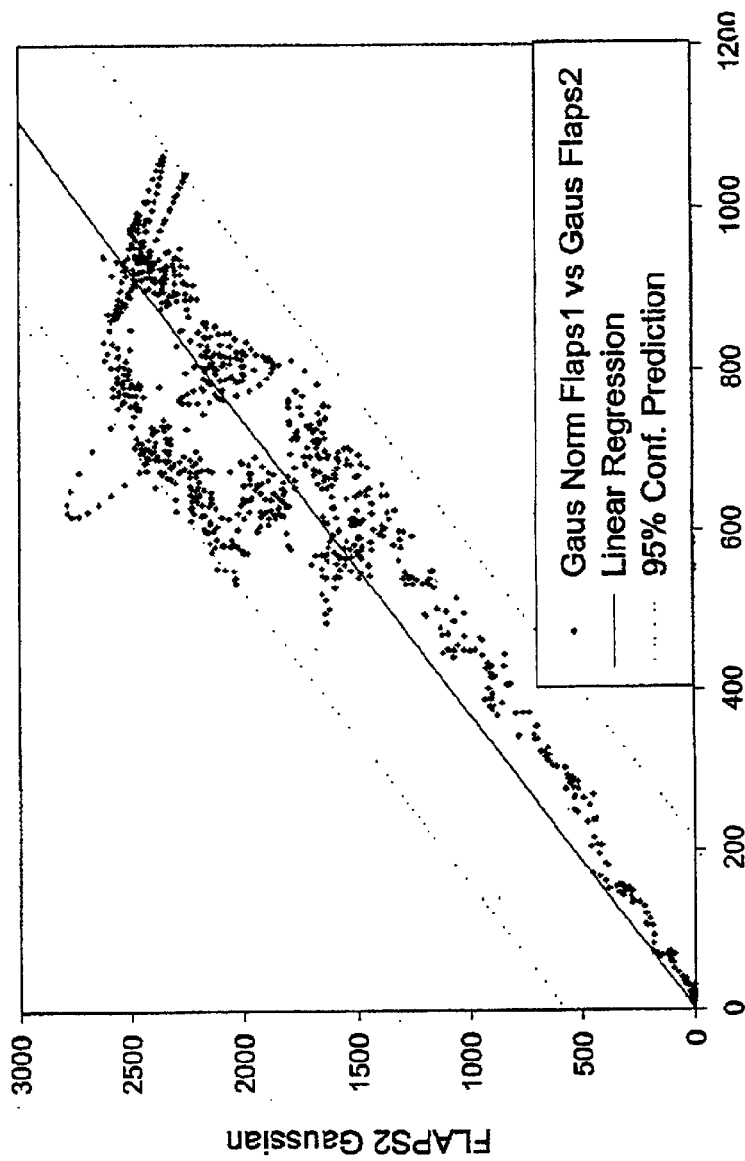

Referring to FIG. 7, since the data sets were not normally distributed, non-parametric statistical methods were used to derive a correlation coefficient (Spearman rank order). A correlation coefficient of 0.86 was obtained, suggesting a good correlation between the fluorescent particles detected by FLAPS1 and FLAPS2, and that the two instruments were measuring the same aerosol cloud in the test chamber and tracking its concentration changes with similar fidelity. Since the laser diode was selected in FLAPS1 while the YAG laser in FLAPS2 was also operating, this correlation suggested that both types of lasers detected the same aerosol cloud. Moreover, during this process, the change in laser in the FLAPS1 apparatus further illustrates that the use of the Nichia laser diode or the HeCd laser were equally effective and exerted no significant effect in the measurements.

Example 5

Previous experiments were performed in an aerosol chamber, which allow controlled studies to be performed reproducibly under similar specified conditions. Biological aerosol detection, however, must perform acceptably in the natural environment under unpredictable conditions. In order to test the system's ability to function in the natural environment, the FLAPS1 instrument was installed in a trailer located in the field. The air intake to the instrument was about 3 meters above the ground.

Reference samplers (slit samplers) were positioned about 10 meters away, also about 3 m above ground level. Although not ideal, as the distance between the systems could contribute to timing errors in tracking dynamic aerosol activity, this set up, under fair weather conditions, has been previously shown to provide acceptable results.

As set forth in FIG. 8, in the presence of a high concentration of BG spore aerosol, visual inspection of the fluorescence signals using the Nichia laser diode (gated % FL) suggests the signals correlate well with viable counts, expressed again as Agent Containing Particles per Liter of Air (ACPLA).

Figure 9:
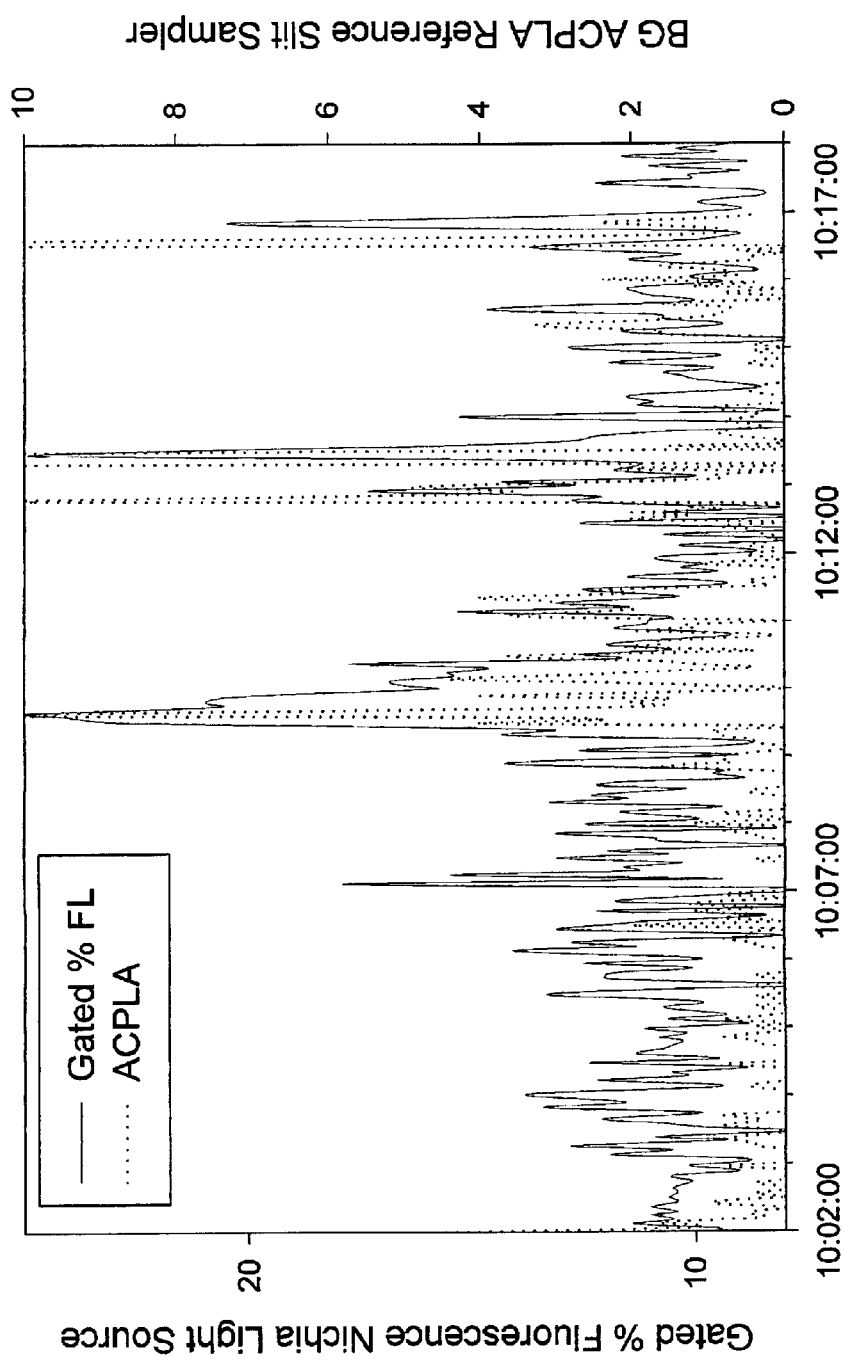
Figure 10:
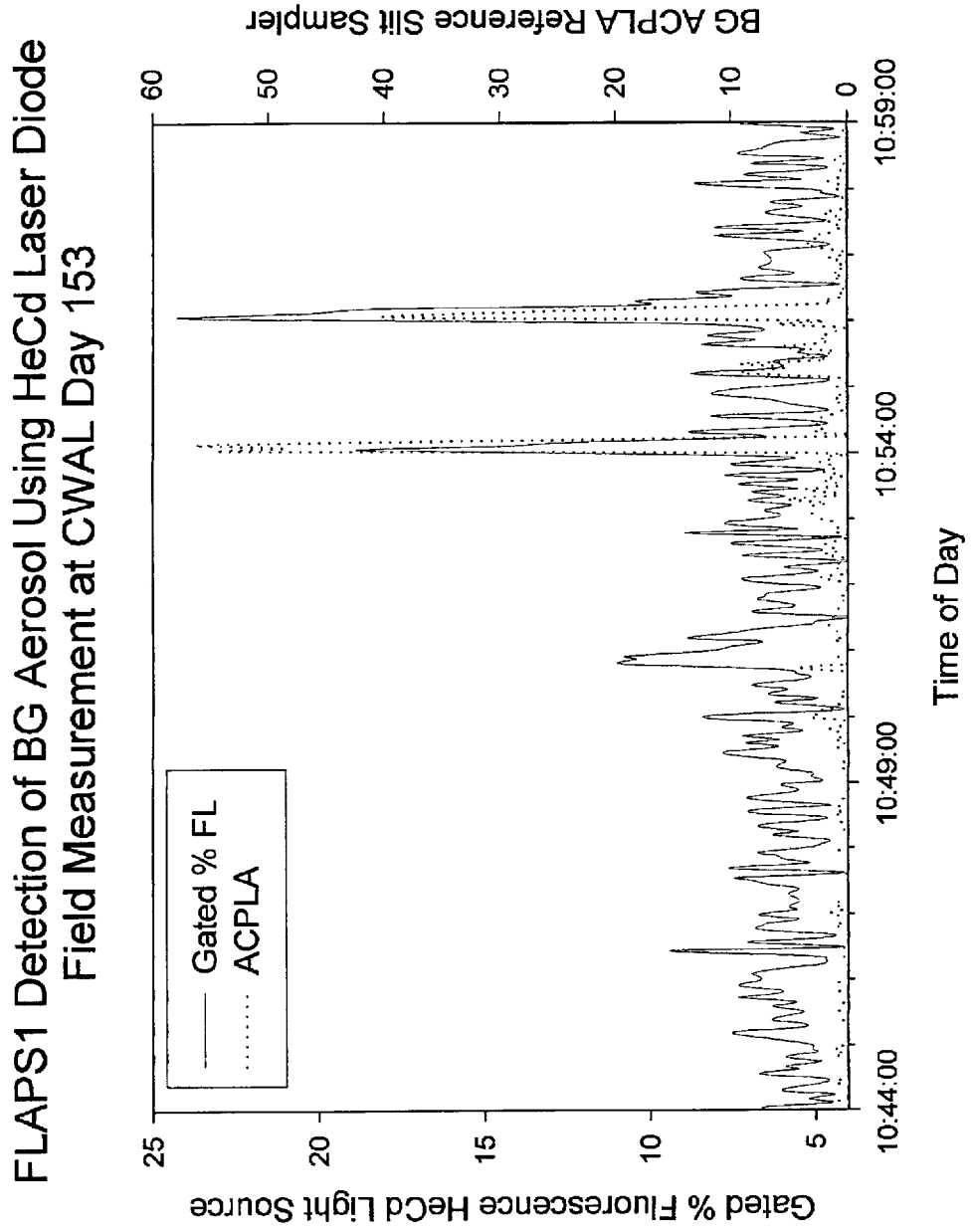

As shown In FIG. 9, repeat testing of the Nichia laser on a second day using low aerosol concentrations (6–10 ACPLA), yielded measurements discernable from background, as did subsequent comparative testing using the HeCd laser as shown in FIG. 10.

Example 6

In practice, a biological detector also measures material that occurs in the background. In the rare instance when an unusual biological cloud appears, the instrument must be capable of registering a discernable difference between the background and the biological cloud. Hence, the background measuring performance of an instrument must be carefully characterized.

Figure 11:
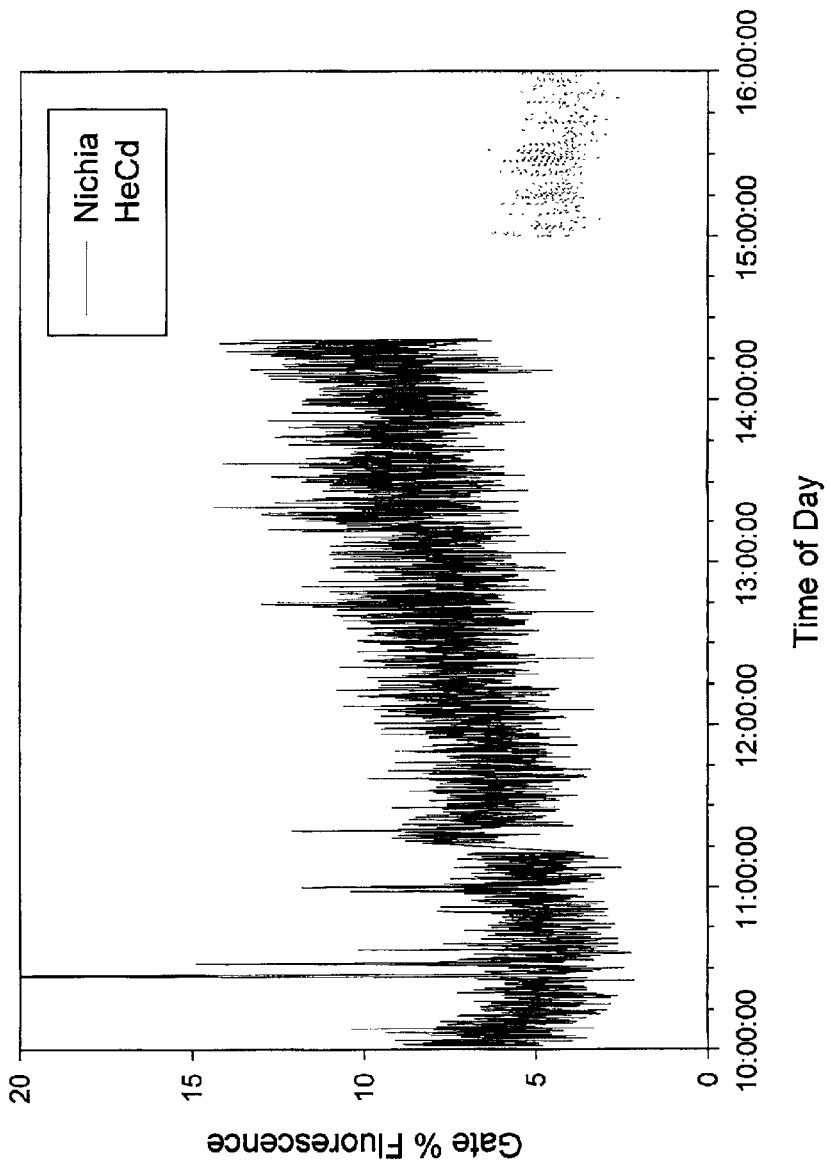

As shown in FIG. 11, measurement of background aerosol was conducted using the FLAPS1 apparatus fitted with a pre-concentration virtual impactor to enhance particle counts presented to its intake. Using the Nichia laser, and over a 4.5 hour sampling period, the fractional background fluorescent population showed only gradual changes. Occasional spikes occurred but were only of short duration.

Similarly, for the latter part of the measurements and switching to the HeCd laser yielded comparable results. The slightly lower fractional levels in the latter trace may be a function of the laser power (15 versus 12 mW) although this has not been verified. Nevertheless, the two measurement systems were within acceptable performance levels, given the influence of environmental variables.

Example 7

Figure 12:
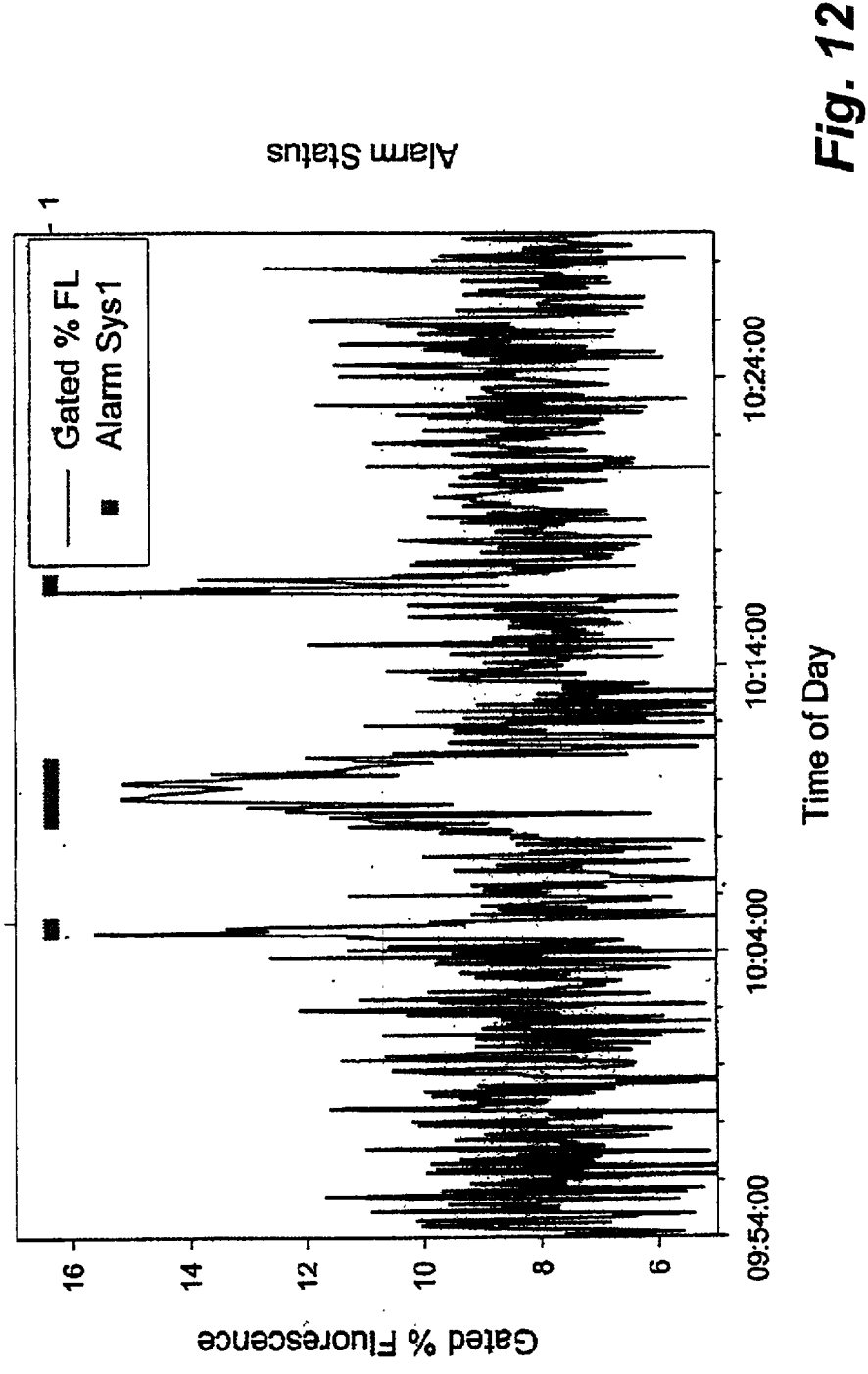
Figure 13:
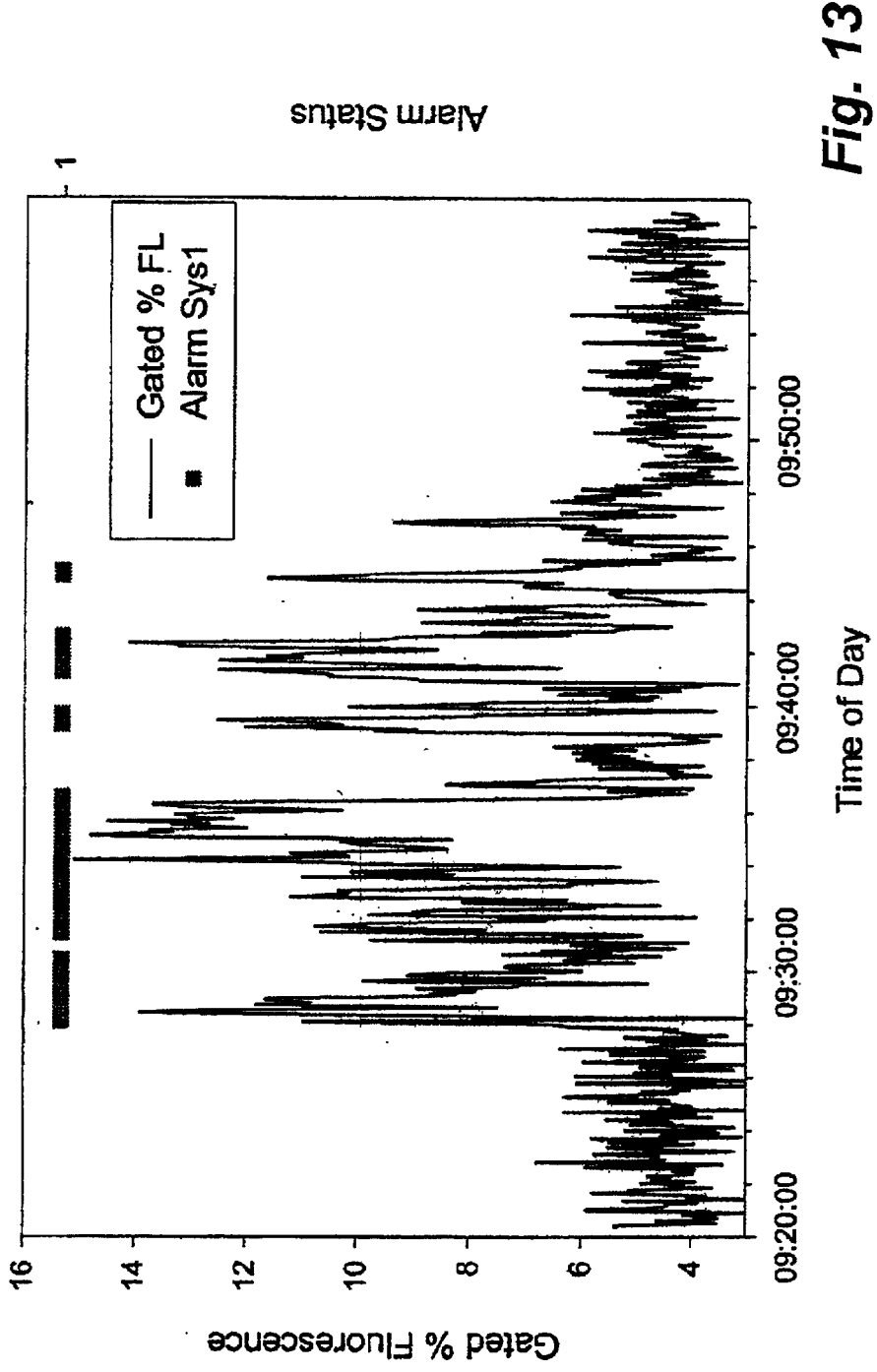

Having reference to FIGS. 12 and 13, biomolecule simulant response trials were performed. Ovalbumin (OV) available from Sigma Chemical Co. was used as a simulant for protein based toxins. In its pure form only short light stimulation at 260–280 nm produces fluorescence from aromatic amino acids present in ovalbumin, per Groves, W. E. F. C. Davies and B. H. Sells. 1968. *Spectrophotometric determination of microgram quantities of protein without nucleic acid interference.* Anal. Biochem 22:195–210. However, as reported in Boulet, C. A., J. Ho, L. Stadnyk, H. G. Thompson, M. R. Spence, G. A. Luoma, R. E. Elaine and W. E. Lee. 1996. *Report on the Canadian Integrated Biological Detection System Trial Results of the Combined Joint Field Trials II, for Biological Detection. Defence Research Establishment Suffield* SR 652 (Unclassified), in previous field trials with OV aerosol using this specific product, excitation with UV light at 340–360 nm produced measurable fluorescence. The material used had a yellowish tinge, on visual inspection, suggesting the presence of egg yolk contaminants which resulted in the fluorescence detected.

Having reference to FIG. 12, OV aerosol was detected using the Nichia laser, producing comparable results and alarm signals to those obtained using the HeCd laser, as shown in FIG. 13. Background noise levels in the test for FIG. 12 were higher than that experienced for FIG. 13 and were most likely due to environmental conditions on the day of testing. Reference data to verify the presence of OV was not available for comparison. Current methodology for collecting OV aerosol utilizing a glass impinger with a time resolution of 5 minutes would have been unsuitable for comparison with FLAPS1 data, the latter having time resolution of 4 seconds.

CONCLUSIONS

The Nichia laser, without the cost, nor the power and technical support requirements of the more conventional gas HeCd or diode pumped solid state YAG lasers, performed equally well. The particular tested laser diode had a wavelength longer that Applicant's experience and thus the results were doubly surprising; first having proved that a low power laser diode can detect biomolecules, and secondly that biomolecules could be excited in particles of interest, even in spores, which could be excited at a larger and longer range of wavelengths that preciously thought practical.

FLAPS1 performance using both the HeCd laser or the Nichia laser diode gave well correlated performance characteristics when presented both with biological aerosol simulants OV and with BG spore aerosol. Spores, by their physiological nature, contain very little biological material and the individual units are no larger than 0.7 μm and are enclosed by a very refractile spore coat. Due to this refractile characteristic, conventional light microscopy of spores reveal very little of its cellular content. In contrast, vegetative cells are better subjects for examination in that they can easily be stained. Thus, performance of biological detectors must be rated by their ability to measure spore aerosols and in these experiments and it has been shown that 10 ACPLA could be detected (FIG. 9).

In the original FLAPS1 design, where HeCd 340–360 nm excitation light was used, it was speculated that the fluorescing molecules were most probably NADH, as shown in FIG. 1. The Nichia laser diode light source emits at about 402 nm, making it possible that the excited molecule is riboflavin, as also illustrated in FIG. 1. In addition, it can be seen that at this wavelength, a small portion at the upper end of NADH excitation spectrum may make a small contribution to the total fluorescent signals. To applicant's knowledge, measurement of riboflavin in spores has not been reported so it is impossible to verify this claim. However, in the literature, autofluorescence from blue and near UV excitation has been reported for a brackish water ciliate that feeds on cyanobacteria (Selbach, M and H. W. Kuhlmann. 1999. *Structure, fluorescent properties and proposed function in phototaxis of the stigma apparatus in the ciliate Chiamydodon mnemosyne*. J. Expl. Biol. 202:919–927.). Also Van Schaik, H. J. C. Alkemade, W. Swart and J. A. Van Best. 1999. *Autofluorescence of the diabetic and healthy human cornea in vivo at different excitation wave-lengths*. Expl Eye Res. 68:1–8 attributed 405 nm excited fluorescence in cornea of diabetes mellitus patients to flavins. Finally, as stated earlier, Solovieva et al. reported isolation of the *Bacillus subtilis* DNA that contained the riboflavin operon and was able to clone in to *E. coli*. At least this suggests that BG has the capability to synthesize riboflavin. Whether the individual spore contains significant amounts of the material is difficult to predict.

Whether the low power laser diodes can detect biomolecules in particles of interest is now proved. Further, laser diodes are becoming available across a larger range of wavelengths. While not all wavelengths are suitable for stimulation of biomolecules, the above examples have demonstrated that the known range should be expanded. Accordingly, it is seen that laser diodes can also be operable at longer wavelengths. The following example illustrates a further and longer wavelength suitable for application when such a laser diode is economically available.

Example 8

An analysis of bacterial stimulation and fluorescence was also conducted at higher wavelengths to further expand the known range of fluorescence of biomolecules, whether or not the biomolecule responsible for the fluorescence is known. An ion laser, model Coherent Enterprise II (Coherent, Inc. of Santa Clara, Calif., USA), was used which produced a wavelength of about 413 nm. Note that the characteristics of the Enterprise II are particularly demonstrative of the disadvantages and of the need for a practical laser diode apparatus. The Enterprise II laser's plasma tube has a suggested life of about 5000 hours and at has a 220 V, single phase maximum power requirement of about 7 kVA. Further, note that the manufacturer, Coherent, Inc., suggests that there are several options are available for keeping the Enterprise II cool for operating at peak performance. About 5 kW of waste heat from the system can be removed with water-to-air or water-to-water heat exchangers, with chillers, or by direct cooling with water that meets our published quality guidelines. The Enterprise II can optionally be cooled with a water-to-air heat exchanger when sufficient water is not available, water quality is poor, or air-cooled operation is desirable. This cooling unit can be located up to 15 meters away and be operated remotely through the power supply control panel.

In the example, particles were contacted and exposed to the ion laser's beam using a Beckman Coulter ELITE™ flow cytometer. For comparison, the flow cytometer was also fitted with a HeCd laser emitting 352 nm for applying the known excitation and response of NADH. The fluidic conditions of the flow cytometer were optimized for smaller particles such as bacteria as the smaller the particle the less they follow the hydrodynamic focusing principle. To maximize the time the particles spend in the sensing area (at the flow cell), the volume flow rate settings were lowered on the flow cytometer. The optimal sheath pressure for acquiring the BG spores was found to be 8.0 psi, with a corresponding sample pressure of approximately 7.2–7.4 psi (based on a 413 nm laser output of 50 mW as the required sample pressure was later found to be dependent on laser power output). Serial dilutions of BG spores were prepared in pure water to yield concentrations of $10^3$–$10^9$/mL. The dilutions were run on the cytometer using the HeCd laser at 351 nm to determine the optimal concentration of BG spores for further experiments. At sheath and sample pressures of 8.0 and 7.2 psi, respectively, the $10^6$/mL concentration yielded the most desirable rate in events/second for data collection.

One of the main objectives of the study was to measure and compare the intrinsic fluorescence of BG spores using the HeCd (352 nm) and the 413 nm light sources. Given that each of the lasers emitted at a different wavelengths, it was necessary to select a filter configuration suitable for the laser light plan and the fluorescence of interest. Accordingly, different filter configurations were used to properly measure the intrinsic fluorescence of BG spores excited by the respective lasers. For the 352 laser, a blocking bandpass filter at 450 nm and a dichroic filter of 505 nm were provided to ensure that excitation light scatter or other artifacts were not detected by the photomultiplier tube (PMT) used to detect emissions in the anticipated range of about 410–540 nm. Similarly, for the 413 laser, a blocking bandpass at 440 nm was provided to ensure only that the PMT only detected fluorescence emissions which were in the anticipated estimated range of 480–570 nm.

Figure 14A:
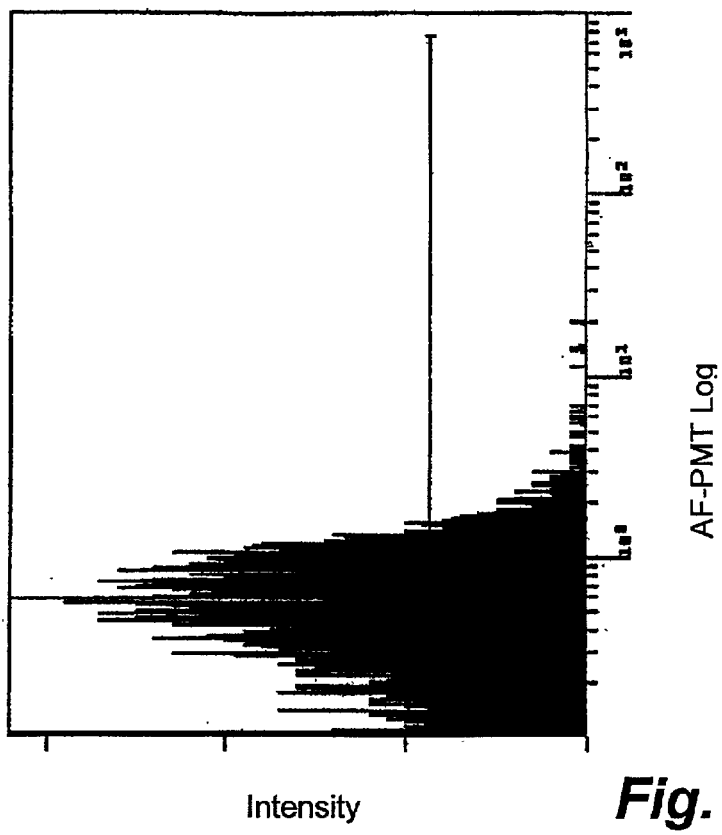
Figure 14B:
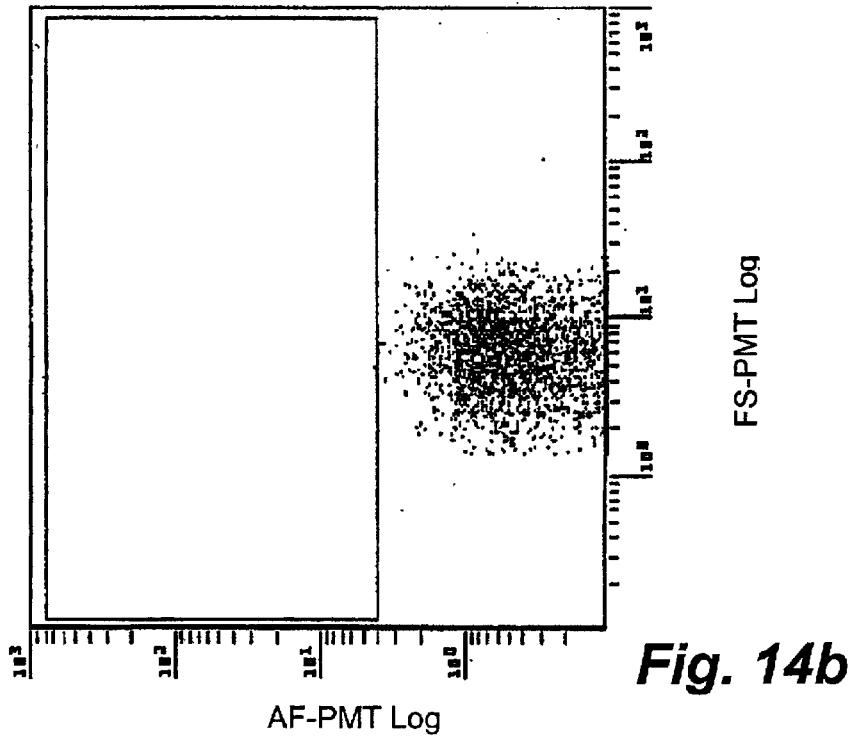
Figure 15A:
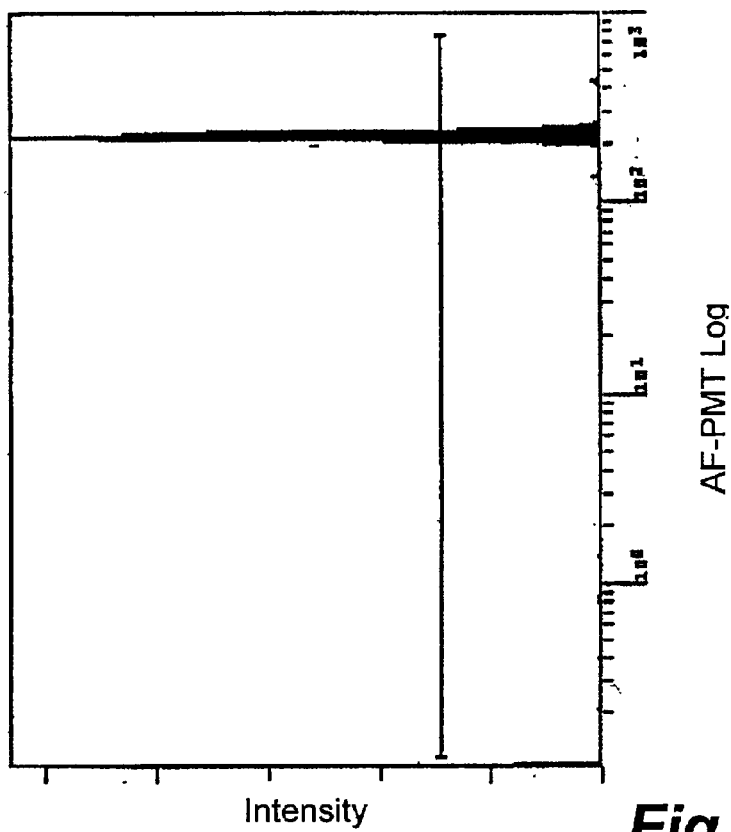
Figure 15B:
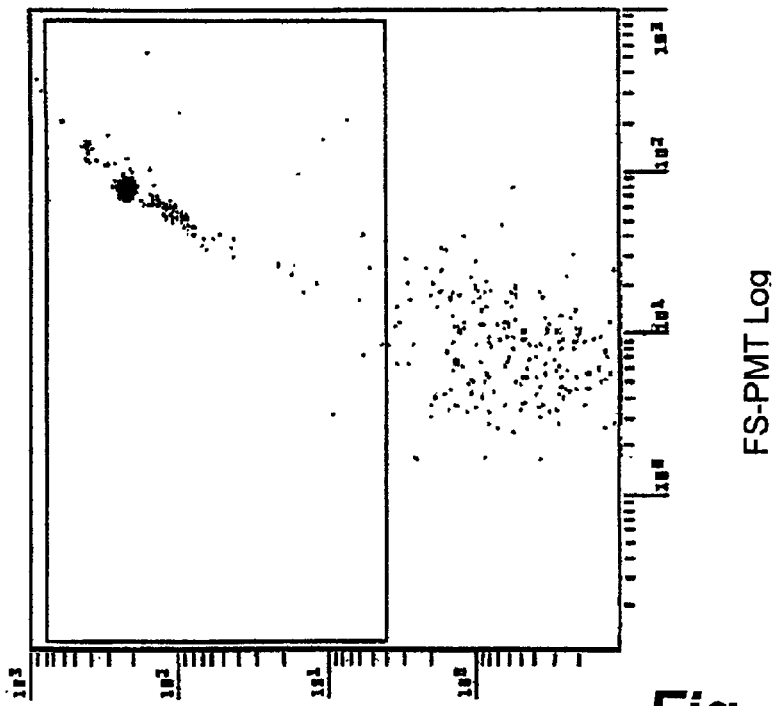

To determine power and fluorescence resolution, a background or negative population was calibrated. As shown in FIGS. 14a and 14b, in a log—log plot of auto-fluorescence PMT (AF-PMT) output vs. forward scatter PMT (FS-PMT), the AF-PMT was adjusted so that a non-fluorescing 1 $\mu$m beads were detected in the first decade of the log scale (about 0.1–30). As shown in FIGS. 15a and 15b, a positive population of 10 $\mu$m fluorescing beads was checked to ensure AF-PMT response across all four log output decades (0.1–1000).

After background fluorescence levels were run and PMT voltage levels were set, the BG spores were run through the cytometer for the 413 laser and for the 352 HeCd laser. The HeCd had a power output of about 30 mW and the 413 nm laser was run at power settings ranging from about 3–50 mW.

Figure 16A:
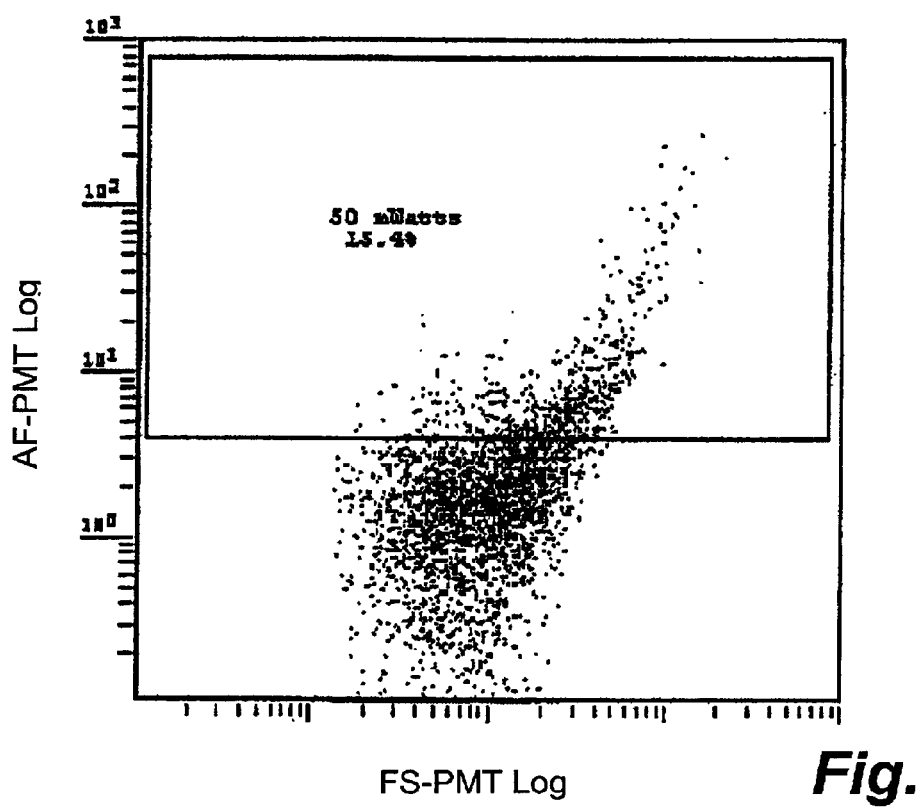
Figure 16B:
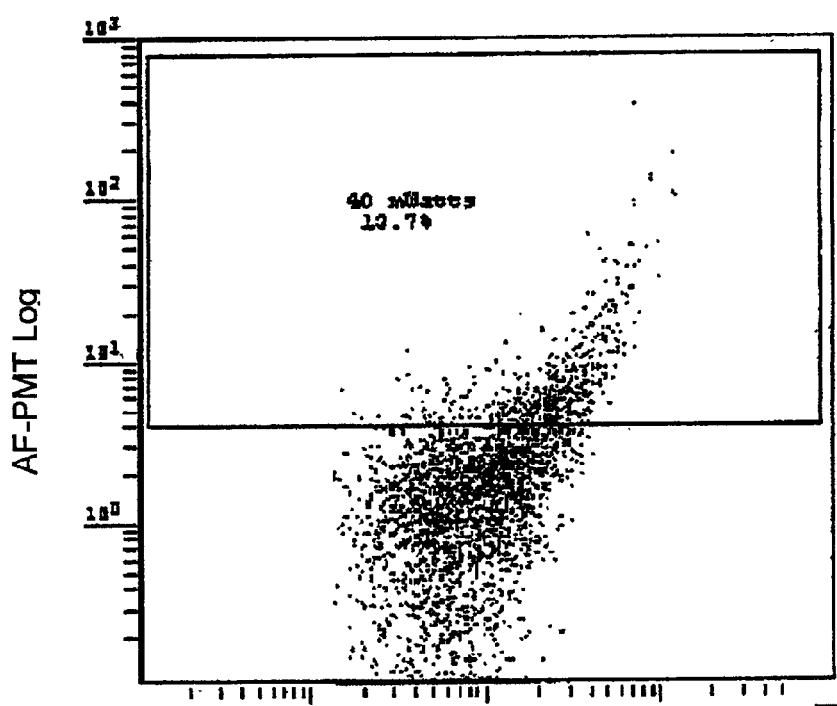
Figure 16C:
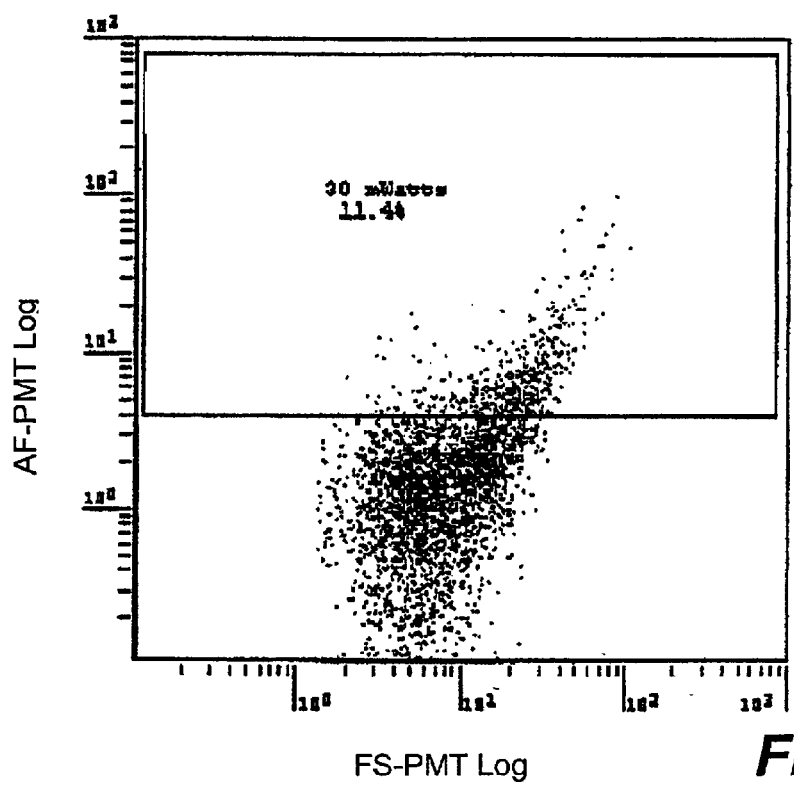
Figure 16D:
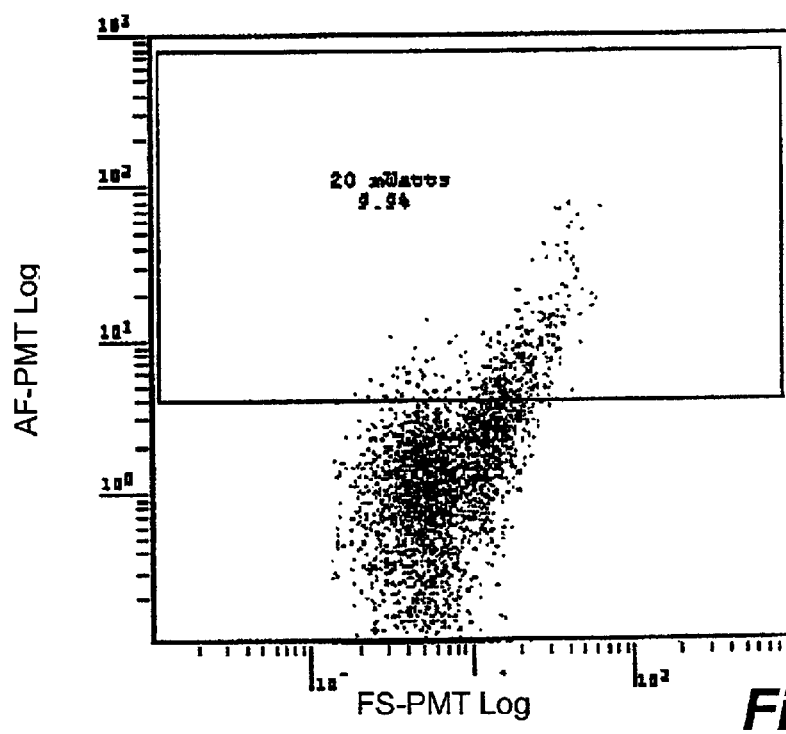
Figure 16E:
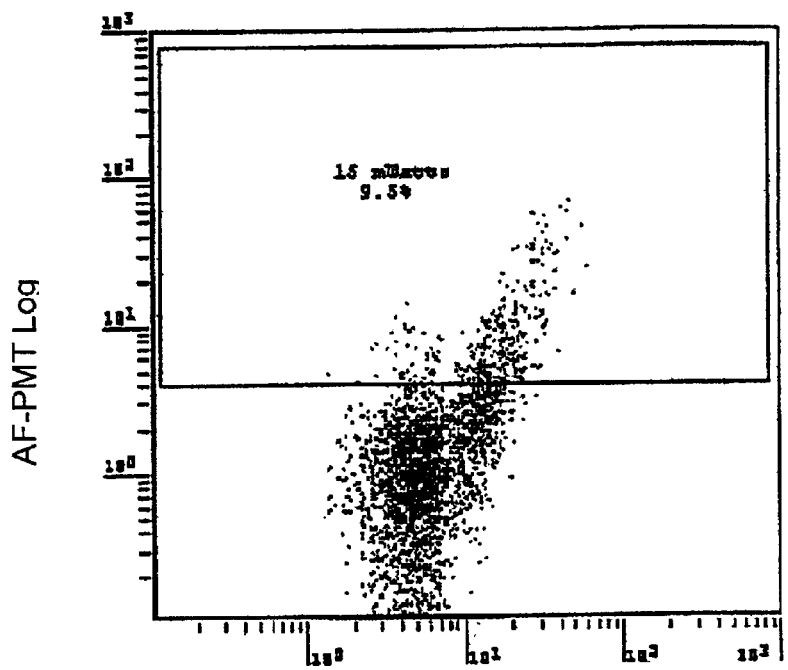
Figure 16F:
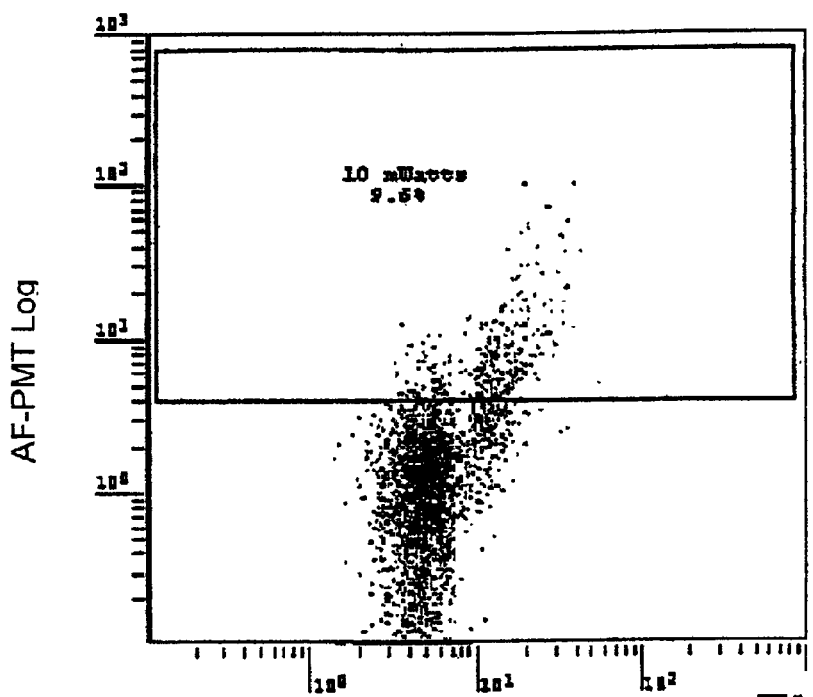
Figure 16G:
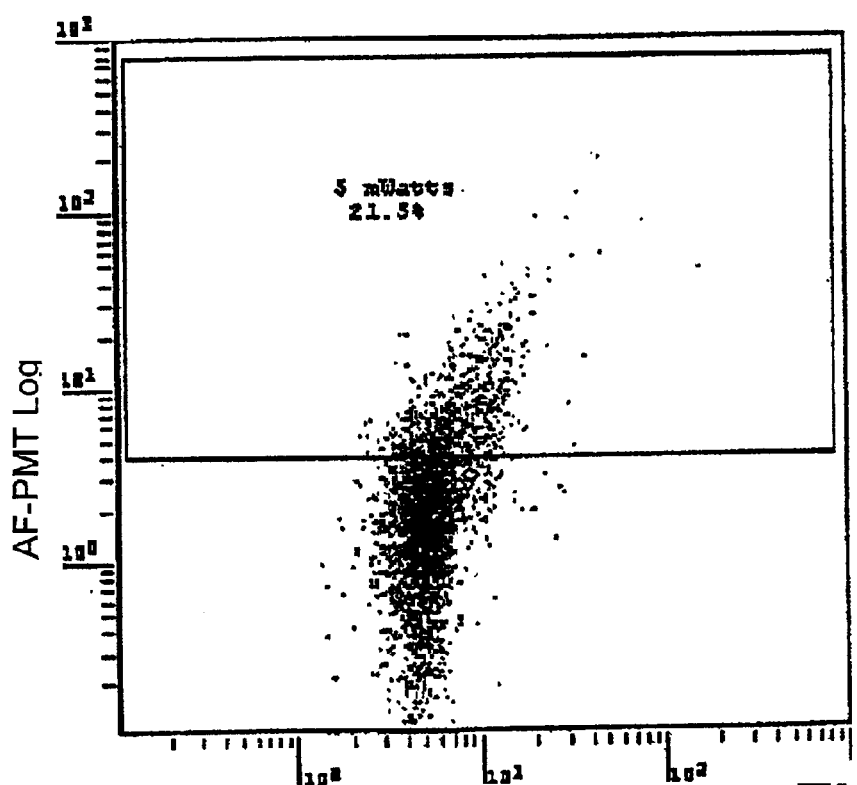

As a measure of BG spore auto-fluorescence, resolution forward scatter was investigated. Using the 413 nm laser, diminishing power levels were applied. Having reference to FIGS. 16a–16g, the resolution of auto-fluorescence was optimal at a power setting of 10 mW. In FIGS. 16a–16e and 16g, higher and lower power settings of 50–15 mW and 5 mW did not produce the same levels of light scattering from BG spores. Light events diminished significantly at power levels below 10 mW. Accordingly, using the cytometer environment, the minimum 413 nm laser power output for obtaining usable fluorescence emission was determined to be about 10 mW (FIG. 16f). The results were similar under repeats tests where new or old spores were used and whether the experiments applied increasing power through 10 mW or reducing power.

For confirmation of the viability detection results and comparison of the light sources applied in the same flow cytometer environment, tests were also conducted with the known NADH biomolecule detecting HeCd laser. Negative and positive populations were applied and the AF-PMT adjusted. With the HeCd laser, instrument noise is prevalent. The FS-PMT peak signal was selected as the discriminating parameter and set accordingly to reduce much of the instrument noise. As shown in FIGS. 17a and 17b, and at HeCd laser power of 30 mW, the prior art laser was similarly able to discern sufficient events to detect auto-fluorescence.

SUMMARY

In summary, we have shown that by using a small, low-power laser diode that emits at 402–405 nm, it is possible to replicate the viability detection performance of the 340–360 nm light sources. Further, having confirmed that fluorescence is detectable at even longer wavelengths (having further applied a conventional 413 nm laser source) then as additional wavelengths of laser diodes become available, they can also be applied in a superior and economical biological detection apparatus.

The findings from this study have critical implications for the future of biological detection, both for military applications as well as in environmental monitoring. With this new inexpensive and compact light source, a detector requires no active cooling system, consumes little power and weighs much less than current instruments. The associated cost reduction not only benefits large industrial and defence applications but also make it possible for commercial and home use.

It is understood that the above description represents the preferred embodiment and that other embodiments are possible including combinations with flow cytometers, cloud chambers and other such apparatus for contacting the particles and the excitation lasers.

The embodiments of the invention in which an exclusive property or privilege is claimed are defined as follows:

1. An improved apparatus for identifying the existence of viable biological particles from a particle population containing a mixture of biologically viable and biologically inert particles, the improvement comprising:
   a solid state excitation source wherein said source is a laser diode for emitting a light beam being directed to contact particles of the particle population and having a wavelength above about 320 nm which is operative to excite biomolecules contained therein to produce fluorescence;
   a photon counter for measuring the intensity of fluorescence emitted from each contacted particle and producing a signal indicative thereof; and
   a microprocessor for comparing each contacted particle's fluorescent intensity signal against predetermined criteria and establishing whether that particle is a biologically viable particle or an inert particle.

2. The improved apparatus of claim 1 wherein the laser diode has a wavelength operative to excite biomolecules from the group consisting of NADH and flavinoids.

3. The improved apparatus of claim 2 wherein the laser diode has a wavelength in the range of about 320 nm to about 420 nm.

4. The improved apparatus of claim 3 wherein the laser diode has a wavelength operative to excite NADH.

5. The improved apparatus of claim 4 wherein the laser diode has a wavelength in the range of about 320 nm to about 360 nm.

6. The improved apparatus of claim 3 wherein the laser diode has a wavelength operative to excite flavinoids.

7. The improved apparatus of claim 6 wherein the laser diode has a wavelength in the range of about 360 nm to about 420 nm.

8. The improved apparatus of claim 6 further comprising:
   means for measuring the size of the contacted particle as indicative of a biological characteristic; and
   means for establishing the contacted particle as a candidate particle if its size is within the range of particles which are respirable.

9. The improved apparatus of claim 8 wherein the size measuring means comprises:
   a sequencer for directing the particles individually and sequentially along a substantially linear path through air;
   an instrument for determining the position of each particle in the airstream as a function of time and the particle's time of flight between two points along the linear path so as to establish the particle's size.

10. The improved apparatus of claim 1 wherein the laser diode light beam is emitted at a power of about 8–15 mW.

11. The improved apparatus of claim 10 wherein the laser diode has a wavelength operative to excite biomolecules from the group consisting of NADH and flavinoids.

12. The improved apparatus of claim 10 wherein the laser diode has a wavelength in the range of about 320 nm to about 420 nm.

13. The improved apparatus of claim 12 wherein the laser diode has a wavelength operative to excite NADH.

14. The improved apparatus of claim 13 wherein the laser diode has a wavelength in the range of about 320 nm to about 360 nm.

15. The improved apparatus of claim 12 wherein the laser diode has a wavelength operative to excite flavinoids.

16. The improved apparatus of claim 15 wherein the laser diode has a wavelength in the range of about 360 nm to about 420 nm.

17. An improved apparatus for identifying the existence of viable biological particles from a particle population containing a mixture of biologically viable and biologically inert particles, the improvement comprising:
   a solid state excitation source wherein said source is a laser diode for emitting a light beam being directed to contact particles of the particle population and having a wavelength above about 320 nm which is operative to excite biomolecules contained therein to produce fluorescence;
   means for measuring the intensity of fluorescence emitted from each particle and producing a signal indicative thereof; and
   means for comparing each particle's fluorescence intensity signal against pre-determined criteria and establishing whether that particle is biologically viable or an inert particle.

18. The improved apparatus of claim 17 wherein the intensity measuring means comprise a photon counter.

19. The improved apparatus of claim 17 wherein the intensity measuring means comprise a microprocessor.

20. A method for identifying the existence of viable biological particles from a particle population containing a mixture of biologically viable and biologically inert particles, the method comprising:

provided a solid state excitation source wherein said source is a laser diode for emitting a light beam having a wavelength from about 320 nm to 500 nm and a detector for measuring fluorescence emission and producing a signal indicative of the intensity thereof;

contacting the laser beam and particles of the population so as to excite biomolecules contained in a contacted particle to produce fluorescence;

using the detector to measure the intensity of fluorescence from the contacted particle;

comparing each particle's fluorescence intensity signal against predetermined criteria and establishing whether that particle is biologically viable or an inert particle.

21. The method of claim 20 further comprising:

measuring the size of the contacted particle as a biological characteristic; and establishing the contacted particle as a candidate particle if its size is within the range of particles which are respirable.

22. The method of claim 20 wherein the laser diode has a wavelength operative to excite biomolecules from the group consisting of NADH and flavinoids.

23. The method of claim 20 wherein the laser diode has a wavelength operative to excite NADH.

24. The method of claim 20 wherein the laser diode has a wavelength operative to excite riboflavin.

* * * * *

Disclaimer

6,831,279 B2 — Jim Yew-Wah Ho, Medicine Hat (CA). LASER DIODE-EXCITED BIOLOGICAL PARTICLE DETECTION SYSTEM. Patent dated December 14, 2004. Disclaimer filed July 16, 2014, by the assignee, TSI, Incorporated.

Hereby disclaims complete claims 1-24 of said patent.

*(Official Gazette, September 2, 2014)*

INTER PARTES REEXAMINATION CERTIFICATE (1011th)
United States Patent
Ho

(10) Number: US 6,831,279 C1
(45) Certificate Issued: Dec. 12, 2014

(54) LASER DIODE-EXCITED BIOLOGICAL PARTICLE DETECTION SYSTEM

(75) Inventor: Jim Yew-Wah Ho, Medicine Hat (CA)

(73) Assignee: TSI Incorporated, Shoreview, MN (US)

Reexamination Request:
No. 95/001,968, Apr. 12, 2012

Reexamination Certificate for:
Patent No.: 6,831,279
Issued: Dec. 14, 2004
Appl. No.: 09/993,488
Filed: Nov. 27, 2001

(51) Int. Cl.
| | |
|---|---|
| B27N 3/00 | (2006.01) |
| C08K 5/205 | (2006.01) |
| C08K 5/00 | (2006.01) |
| C08G 18/64 | (2006.01) |
| C08G 18/00 | (2006.01) |
| C08L 97/02 | (2006.01) |
| C08G 18/76 | (2006.01) |
| C08G 18/28 | (2006.01) |
| C08L 97/00 | (2006.01) |

(52) U.S. Cl.
USPC .................................. 250/458.1; 250/461.2

(58) Field of Classification Search
None
See application file for complete search history.

(56) References Cited

To view the complete listing of prior art documents cited during the proceeding for Reexamination Control Number 95/001,968, please refer to the USPTO's public Patent Application Information Retrieval (PAIR) system under the Display References tab.

*Primary Examiner* — Behzad Peikari

(57) ABSTRACT

Apparatus is provided for detection of viable and potentially hazardous biological particles in a population which may be dispersed in fluid flow. The particles are characterized as biological and viable by contacting particles with laser light from a laser diode and then looking for the emission of fluorescence which is typically emitted from bacteria or bacterial spore. Biomolecules which are representative of viability are now known to be excited in range of 320 nm and longer. The resulting apparatus is economical, compact and has low-power requirements enabling portable operation. Preferably, the laser diode is combined with an aerodynamic particle sizer to separate particles for sequential contacts, or with additional timing lasers for establishing particle size.

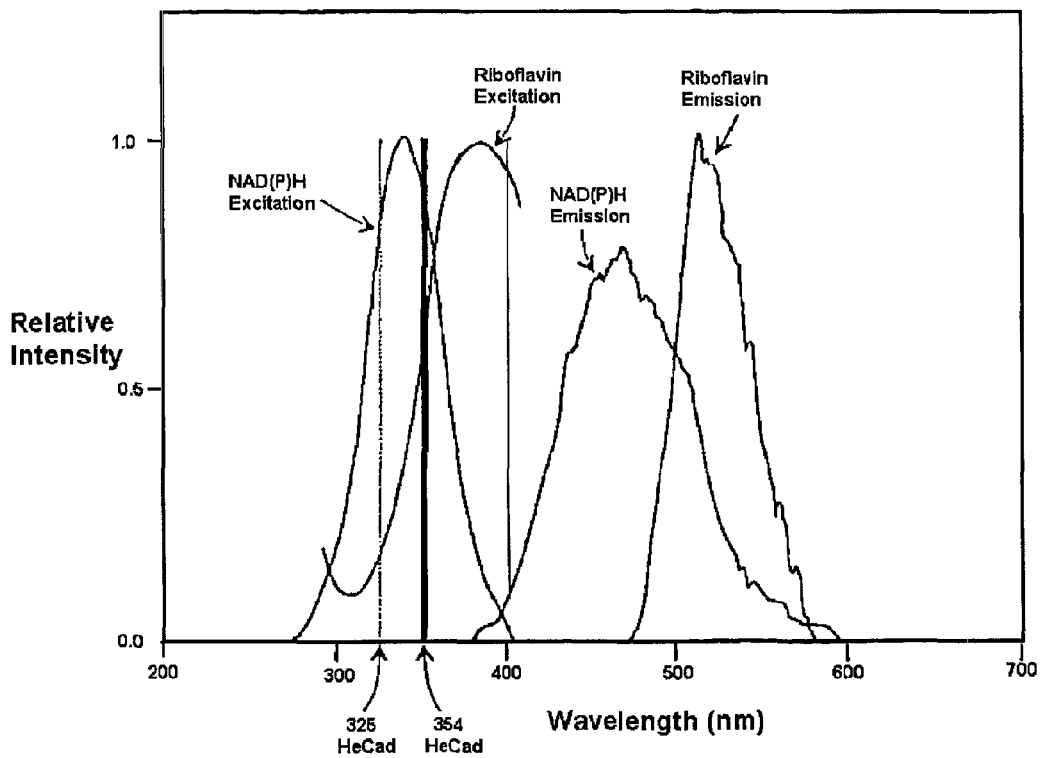

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-24 are now disclaimed.

\* \* \* \* \*